(12) United States Patent
Ericsson et al.

(10) Patent No.: US 8,664,164 B2
(45) Date of Patent: Mar. 4, 2014

(54) PROBES FOR SPECIFIC ANALYSIS OF NUCLEIC ACIDS

(75) Inventors: Olof Ericsson, Uppsala (SE); Magnus Isaksson, Uppsala (SE); Henrik Johansson, Uppsala (SE); Ulf Landegren, Uppsala (SE)

(73) Assignee: Agilent Technologies, Inc., Santa Clara, CA (US)

(*) Notice: Subject to any disclaimer, the term of this patent is extended or adjusted under 35 U.S.C. 154(b) by 0 days.

(21) Appl. No.: 13/384,990

(22) PCT Filed: Jul. 23, 2010

(86) PCT No.: PCT/EP2010/060715
§ 371 (c)(1),
(2), (4) Date: May 16, 2012

(87) PCT Pub. No.: WO2011/009941
PCT Pub. Date: Jan. 27, 2011

(65) Prior Publication Data
US 2012/0220479 A1 Aug. 30, 2012

(30) Foreign Application Priority Data
Jul. 23, 2009 (GB) .................................. 0912909.9

(51) Int. Cl.
*C12Q 1/68* (2006.01)
*C40B 30/04* (2006.01)
*C12N 15/09* (2006.01)
*C12Q 1/44* (2006.01)

(52) U.S. Cl.
USPC ........... 506/7; 536/24.2; 536/24.33; 435/91.2

(58) Field of Classification Search
USPC .......................................................... 506/7
See application file for complete search history.

(56) References Cited

U.S. PATENT DOCUMENTS

| 4,336,173 A | 6/1982 | Ugelstad |
| 2006/0292597 A1 | 12/2006 | Shapero et al. |

FOREIGN PATENT DOCUMENTS

| EP | 1 350 853 A1 | 10/2003 |
| WO | 98/40518 A2 | 9/1998 |
| WO | 2005/111236 A1 | 11/2005 |
| WO | 2008/153492 A1 | 12/2008 |

OTHER PUBLICATIONS

Padegimas et al., Analytical Biochemistry, 1998, 260, pp. 149-153.*
International Search Report from PCT/EP2010/060715 dated Sep. 22, 2010 (3 pages).

(Continued)

*Primary Examiner* — Larry Riggs
*Assistant Examiner* — Karla Dines

(57) ABSTRACT

The present invention provides a method for detecting or enriching for a target deoxyribonucleic acid (DNA) present in a nucleic acid sample, said method comprising: (a) fragmenting a nucleic acid sample to generate nucleic acid fragments including a target fragment containing said target DNA and non-specifically ligating an adaptor sequence to an end of said fragments; (b) rendering said fragments at least partially single-stranded; (c) contacting the at least partially single-stranded fragments of step (b) with oligonucleotides A and B of a single target-specific nucleic acid probe; (d) ligating oligonucleotide B of said probe to the part of the single-stranded portion of said target fragment which is hybridised to oligonucleotide A of said probe to produce a probe-target fragment hybrid; and (e) detecting or enriching for said probe-target fragment hybrid.

18 Claims, 3 Drawing Sheets

(56) References Cited

OTHER PUBLICATIONS

Figure 1:
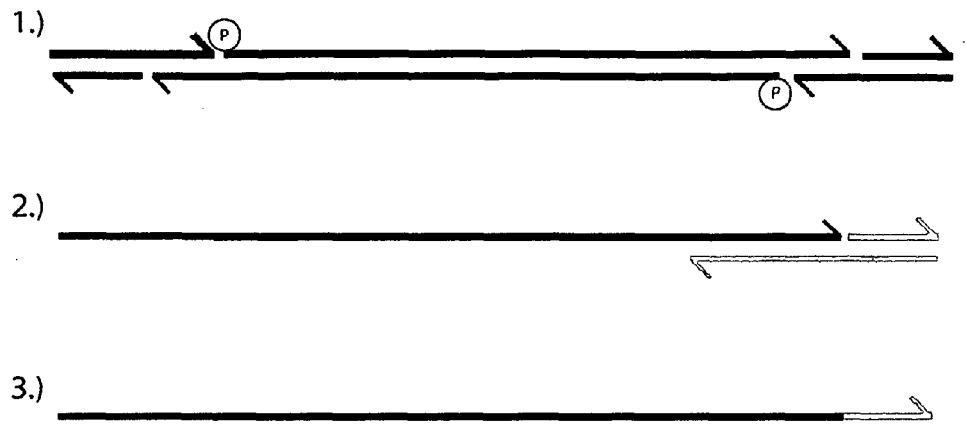

Written Opinion from PCT/EP2010/060715 dated Sep. 22, 2010 (10 pages).

Callow, Matthew J. et al.; "Selective DNA amplification from complex genomes using universal double-sided adapters"; Nucleic Acids Research 2004, vol. 32, No. 2 E21 (6 pages).

Communication pursuant to Article 94(3) EPC for European application No. 10 736 709.6, dated Mar. 28, 2013, 5 pages.

\* cited by examiner

1.)

2.)

3.)

4.)

1.)

2.)

3.)

4.)

5.)

SEQUENCE LISTING

```
<160> NUMBER OF SEQ ID NOS: 70

<210> SEQ ID NO 1
<211> LENGTH: 60
<212> TYPE: DNA
<213> ORGANISM: Artificial sequence
<220> FEATURE:
<223> OTHER INFORMATION: Probe-oligonucleotide A ROI 1

<400> SEQUENCE: 1
acaacgggaa ttcaaatcaa gatggtggcc acacccatg cgtaccaatg gatgcggtct      60

<210> SEQ ID NO 2
<211> LENGTH: 60
<212> TYPE: DNA
<213> ORGANISM: Artificial sequence
<220> FEATURE:
<223> OTHER INFORMATION: Probe-oligonucleotide A ROI 2

<400> SEQUENCE: 2
aaaagaagca gggagtcaac ttcctgcacc tttaactcta cgtaccaatg gatgcggtct      60

<210> SEQ ID NO 3
<211> LENGTH: 60
<212> TYPE: DNA
<213> ORGANISM: Artificial sequence
<220> FEATURE:
<223> OTHER INFORMATION: Probe-oligonucleotide A ROI 3

<400> SEQUENCE: 3
cacctgatga tggtcmtgga ggcattgttc tgattctttg cgtaccaatg gatgcggtct      60

<210> SEQ ID NO 4
<211> LENGTH: 60
<212> TYPE: DNA
<213> ORGANISM: Artificial sequence
<220> FEATURE:
<223> OTHER INFORMATION: Probe-oligonucleotide A ROI 4

<400> SEQUENCE: 4
```

```
cacacaccag acttgtcagc ctcccaaaga gccatgctcc cgtaccaatg gatgcggtct    60
```

<210> SEQ ID NO 5
<211> LENGTH: 60
<212> TYPE: DNA
<213> ORGANISM: Artificial sequence
<220> FEATURE:
<223> OTHER INFORMATION: Probe-oligonucleotide A ROI 5

<400> SEQUENCE: 5

```
cactggctga ggtgccagat gggtctcctg gctataggga cgtaccaatg gatgcggtct    60
```

<210> SEQ ID NO 6
<211> LENGTH: 60
<212> TYPE: DNA
<213> ORGANISM: Artificial sequence
<220> FEATURE:
<223> OTHER INFORMATION: Probe-oligonucleotide A ROI 6

<400> SEQUENCE: 6

```
tcttcaaagg caaggtttca attatgcaaa aaccacctta cgtaccaatg gatgcggtct    60
```

<210> SEQ ID NO 7
<211> LENGTH: 60
<212> TYPE: DNA
<213> ORGANISM: Artificial sequence
<220> FEATURE:
<223> OTHER INFORMATION: Probe-oligonucleotide A ROI 7

<400> SEQUENCE: 7

```
aayctacggc catggcaggt aagacgctgc agggaagcag cgtaccaatg gatgcggtct    60
```

<210> SEQ ID NO 8
<211> LENGTH: 60
<212> TYPE: DNA
<213> ORGANISM: Artificial sequence
<220> FEATURE:
<223> OTHER INFORMATION: Probe-oligonucleotide A ROI 8

<400> SEQUENCE: 8

```
tgctgtttcc acatagcaga ggctgttagg ctcagagcta cgtaccaatg gatgcggtct    60
```

<210> SEQ ID NO 9
<211> LENGTH: 60
<212> TYPE: DNA
<213> ORGANISM: Artificial sequence
<220> FEATURE:
<223> OTHER INFORMATION: Probe-oligonucleotide A ROI 9

<400> SEQUENCE: 9

```
ggggtgcttg agagcttcgc ttgcacttat tcgccaacta cgtaccaatg gatgcggtct    60
```

<210> SEQ ID NO 10
<211> LENGTH: 60
<212> TYPE: DNA
<213> ORGANISM: Artificial sequence
<220> FEATURE:
<223> OTHER INFORMATION: Probe-oligonucleotide A ROI 10

<400> SEQUENCE: 10

```
tctgtggtag tacctagaat aagctatgca gcctctctga cgtaccaatg gatgcggtct    60
```

<210> SEQ ID NO 11
<211> LENGTH: 60
<212> TYPE: DNA
<213> ORGANISM: Artificial sequence

```
<220> FEATURE:
<223> OTHER INFORMATION: Probe-oligonucleotide A ROI 11

<400> SEQUENCE: 11
gacagccgtg tattacccaa tatccccaaa ggcagcctta cgtaccaatg gatgcggtct    60

<210> SEQ ID NO 12
<211> LENGTH: 60
<212> TYPE: DNA
<213> ORGANISM: Artificial sequence
<220> FEATURE:
<223> OTHER INFORMATION: Probe-oligonucleotide A ROI 12

<400> SEQUENCE: 12
ggttctgctc ctcatccgct gtggatcaga tgtgctctga cgtaccaatg gatgcggtct    60

<210> SEQ ID NO 13
<211> LENGTH: 60
<212> TYPE: DNA
<213> ORGANISM: Artificial sequence
<220> FEATURE:
<223> OTHER INFORMATION: Probe-oligonucleotide A ROI 13

<400> SEQUENCE: 13
aatcttttgg aacccaattg gtcatatttc cttctactta cgtaccaatg gatgcggtct    60

<210> SEQ ID NO 14
<211> LENGTH: 60
<212> TYPE: DNA
<213> ORGANISM: Artificial sequence
<220> FEATURE:
<223> OTHER INFORMATION: Probe-oligonucleotide A ROI 14

<400> SEQUENCE: 14
tgctggttct caaatccgaa cgctctgtga taaatttctg cgtaccaatg gatgcggtct    60

<210> SEQ ID NO 15
<211> LENGTH: 60
<212> TYPE: DNA
<213> ORGANISM: Artificial sequence
<220> FEATURE:
<223> OTHER INFORMATION: Probe-oligonucleotide A ROI 15

<400> SEQUENCE: 15
ctcacagaaa ccaaagcgtt tcccaacagc acgtttcctg cgtaccaatg gatgcggtct    60

<210> SEQ ID NO 16
<211> LENGTH: 60
<212> TYPE: DNA
<213> ORGANISM: Artificial sequence
<220> FEATURE:
<223> OTHER INFORMATION: Probe-oligonucleotide A ROI 16

<400> SEQUENCE: 16
aattttagaa atccttraat tttccatgtc tacattcatg cgtaccaatg gatgcggtct    60

<210> SEQ ID NO 17
<211> LENGTH: 60
<212> TYPE: DNA
<213> ORGANISM: Artificial sequence
<220> FEATURE:
<223> OTHER INFORMATION: Probe-oligonucleotide A ROI 17

<400> SEQUENCE: 17
gttctatgaa aagaaaaaaa gaaacgatta aggtttcatg cgtaccaatg gatgcggtct    60
```

```
<210> SEQ ID NO 18
<211> LENGTH: 20
<212> TYPE: DNA
<213> ORGANISM: Artificial sequence
<220> FEATURE:
<223> OTHER INFORMATION: Adaptor amine plus

<400> SEQUENCE: 18
cgttatcaac ctgggtccga                                              20

<210> SEQ ID NO 19
<211> LENGTH: 21
<212> TYPE: DNA
<213> ORGANISM: Artificial sequence
<220> FEATURE:
<223> OTHER INFORMATION: Adaptor amine minus

<400> SEQUENCE: 19
tcggacccag gttgataacg t                                            21

<210> SEQ ID NO 20
<211> LENGTH: 40
<212> TYPE: DNA
<213> ORGANISM: Artificial sequence
<220> FEATURE:
<223> OTHER INFORMATION: Probe-oligonucleotide B

<400> SEQUENCE: 20
ctggacctta atcgtgtgcg agaccgcatc cattggtacg                        40

<210> SEQ ID NO 21
<211> LENGTH: 20
<212> TYPE: DNA
<213> ORGANISM: Artificial sequence
<220> FEATURE:
<223> OTHER INFORMATION: Common primer forward

<400> SEQUENCE: 21
agaccgcatc cattggtacg                                              20

<210> SEQ ID NO 22
<211> LENGTH: 20
<212> TYPE: DNA
<213> ORGANISM: Artificial sequence
<220> FEATURE:
<223> OTHER INFORMATION: Common primer reverse

<400> SEQUENCE: 22
tcggacccag gttgataacg                                              20

<210> SEQ ID NO 23
<211> LENGTH: 18
<212> TYPE: DNA
<213> ORGANISM: Artificial sequence
<220> FEATURE:
<223> OTHER INFORMATION: P1 forward

<400> SEQUENCE: 23
ttccccactg acagcctc                                                18

<210> SEQ ID NO 24
<211> LENGTH: 19
<212> TYPE: DNA
<213> ORGANISM: Artificial sequence
<220> FEATURE:
<223> OTHER INFORMATION: P1 reverse

<400> SEQUENCE: 24
```

-continued gacccaaaac ccaaaatgg                                        19

<210> SEQ ID NO 25
<211> LENGTH: 18
<212> TYPE: DNA
<213> ORGANISM: Artificial sequence
<220> FEATURE:
<223> OTHER INFORMATION: P2 forward

<400> SEQUENCE: 25
cccctgtgga cctcaacc                                         18

<210> SEQ ID NO 26
<211> LENGTH: 18
<212> TYPE: DNA
<213> ORGANISM: Artificial sequence
<220> FEATURE:
<223> OTHER INFORMATION: P2 reverse

<400> SEQUENCE: 26
tgcttgaaaa gccagtgc                                         18

<210> SEQ ID NO 27
<211> LENGTH: 21
<212> TYPE: DNA
<213> ORGANISM: Artificial sequence
<220> FEATURE:
<223> OTHER INFORMATION: P3 forward

<400> SEQUENCE: 27
tcacggaggc attctaaagt c                                     21

<210> SEQ ID NO 28
<211> LENGTH: 18
<212> TYPE: DNA
<213> ORGANISM: Artificial sequence
<220> FEATURE:
<223> OTHER INFORMATION: P3 reverse

<400> SEQUENCE: 28
ttgatgcccc caagaatc                                         18

<210> SEQ ID NO 29
<211> LENGTH: 18
<212> TYPE: DNA
<213> ORGANISM: Artificial sequence
<220> FEATURE:
<223> OTHER INFORMATION: P4 forward

<400> SEQUENCE: 29
ccaagggcat ccagtttg                                         18

<210> SEQ ID NO 30
<211> LENGTH: 18
<212> TYPE: DNA
<213> ORGANISM: Artificial sequence
<220> FEATURE:
<223> OTHER INFORMATION: P4 reverse

<400> SEQUENCE: 30
ggggccacac acatcttc                                         18

<210> SEQ ID NO 31
<211> LENGTH: 18
<212> TYPE: DNA
<213> ORGANISM: Artificial sequence

```
<220> FEATURE:
<223> OTHER INFORMATION: P5 forward

<400> SEQUENCE: 31
accttccttg cccctctg                                                18

<210> SEQ ID NO 32
<211> LENGTH: 18
<212> TYPE: DNA
<213> ORGANISM: Artificial sequence
<220> FEATURE:
<223> OTHER INFORMATION: P5 reverse

<400> SEQUENCE: 32
tccagccgtc aactcctc                                                18

<210> SEQ ID NO 33
<211> LENGTH: 19
<212> TYPE: DNA
<213> ORGANISM: Artificial sequence
<220> FEATURE:
<223> OTHER INFORMATION: P6 forward

<400> SEQUENCE: 33
tgagcaaatc cagtcaggg                                               19

<210> SEQ ID NO 34
<211> LENGTH: 18
<212> TYPE: DNA
<213> ORGANISM: Artificial sequence
<220> FEATURE:
<223> OTHER INFORMATION: P6 reverse

<400> SEQUENCE: 34
actgtgtggc aaactgcg                                                18

<210> SEQ ID NO 35
<211> LENGTH: 19
<212> TYPE: DNA
<213> ORGANISM: Artificial sequence
<220> FEATURE:
<223> OTHER INFORMATION: P7 forward

<400> SEQUENCE: 35
tgaaaagaga acatggggg                                               19

<210> SEQ ID NO 36
<211> LENGTH: 18
<212> TYPE: DNA
<213> ORGANISM: Artificial sequence
<220> FEATURE:
<223> OTHER INFORMATION: P7 reverse

<400> SEQUENCE: 36
gagaagccct ttccaggc                                                18

<210> SEQ ID NO 37
<211> LENGTH: 18
<212> TYPE: DNA
<213> ORGANISM: Artificial sequence
<220> FEATURE:
<223> OTHER INFORMATION: P8 forward

<400> SEQUENCE: 37
ctcacctttg cgcctctg                                                18
```

-continued

<210> SEQ ID NO 38
<211> LENGTH: 18
<212> TYPE: DNA
<213> ORGANISM: Artificial sequence
<220> FEATURE:
<223> OTHER INFORMATION: P8 reverse

<400> SEQUENCE: 38
gaggtggaga aacgcagg                                                 18

<210> SEQ ID NO 39
<211> LENGTH: 18
<212> TYPE: DNA
<213> ORGANISM: Artificial sequence
<220> FEATURE:
<223> OTHER INFORMATION: P9 forward

<400> SEQUENCE: 39
gcgaagctct caagcacc                                                 18

<210> SEQ ID NO 40
<211> LENGTH: 20
<212> TYPE: DNA
<213> ORGANISM: Artificial sequence
<220> FEATURE:
<223> OTHER INFORMATION: P9 reverse

<400> SEQUENCE: 40
cattgagtct ggagtggagc                                               20

<210> SEQ ID NO 41
<211> LENGTH: 18
<212> TYPE: DNA
<213> ORGANISM: Artificial sequence
<220> FEATURE:
<223> OTHER INFORMATION: P10 forward

<400> SEQUENCE: 41
ctcctctgtg caggtggg                                                 18

<210> SEQ ID NO 42
<211> LENGTH: 18
<212> TYPE: DNA
<213> ORGANISM: Artificial sequence
<220> FEATURE:
<223> OTHER INFORMATION: P10 reverse

<400> SEQUENCE: 42
ggatgtcctc aagccgtg                                                 18

<210> SEQ ID NO 43
<211> LENGTH: 18
<212> TYPE: DNA
<213> ORGANISM: Artificial sequence
<220> FEATURE:
<223> OTHER INFORMATION: P11 forward

<400> SEQUENCE: 43
ggaaactccc cttacccg                                                 18

<210> SEQ ID NO 44
<211> LENGTH: 18
<212> TYPE: DNA
<213> ORGANISM: Artificial sequence
<220> FEATURE:
<223> OTHER INFORMATION: P11 reverse

<400> SEQUENCE: 44

-continued tgttgcccat gtcagcac                                                18

<210> SEQ ID NO 45
<211> LENGTH: 18
<212> TYPE: DNA
<213> ORGANISM: Artificial sequence
<220> FEATURE:
<223> OTHER INFORMATION: P12 forward

<400> SEQUENCE: 45
gtcccatggt gcttgcag                                                18

<210> SEQ ID NO 46
<211> LENGTH: 18
<212> TYPE: DNA
<213> ORGANISM: Artificial sequence
<220> FEATURE:
<223> OTHER INFORMATION: P12 reverse

<400> SEQUENCE: 46
atctctggct ccgtcgtg                                                18

<210> SEQ ID NO 47
<211> LENGTH: 18
<212> TYPE: DNA
<213> ORGANISM: Artificial sequence
<220> FEATURE:
<223> OTHER INFORMATION: P13 forward

<400> SEQUENCE: 47
tttgacgggc atcctttc                                                18

<210> SEQ ID NO 48
<211> LENGTH: 18
<212> TYPE: DNA
<213> ORGANISM: Artificial sequence
<220> FEATURE:
<223> OTHER INFORMATION: P13  reverse

<400> SEQUENCE: 48
acaggcgaag gaggtgtg                                                18

<210> SEQ ID NO 49
<211> LENGTH: 18
<212> TYPE: DNA
<213> ORGANISM: Artificial sequence
<220> FEATURE:
<223> OTHER INFORMATION: P14 forward

<400> SEQUENCE: 49
gtgacctgcc acctccag                                                18

<210> SEQ ID NO 50
<211> LENGTH: 18
<212> TYPE: DNA
<213> ORGANISM: Artificial sequence
<220> FEATURE:
<223> OTHER INFORMATION: P14 reverse

<400> SEQUENCE: 50
gctggcgtaa aggtgagg                                                18

<210> SEQ ID NO 51
<211> LENGTH: 18
<212> TYPE: DNA
<213> ORGANISM: Artificial sequence

```
<220> FEATURE:
<223> OTHER INFORMATION: P15 forward

<400> SEQUENCE: 51
aatggcaacg acgggtag                                                 18

<210> SEQ ID NO 52
<211> LENGTH: 19
<212> TYPE: DNA
<213> ORGANISM: Artificial sequence
<220> FEATURE:
<223> OTHER INFORMATION: P15 reverse

<400> SEQUENCE: 52
caaacgctct gagacagcc                                                19

<210> SEQ ID NO 53
<211> LENGTH: 18
<212> TYPE: DNA
<213> ORGANISM: Artificial sequence
<220> FEATURE:
<223> OTHER INFORMATION: P16 forward

<400> SEQUENCE: 53
gcctggcaga gctgaatc                                                 18

<210> SEQ ID NO 54
<211> LENGTH: 20
<212> TYPE: DNA
<213> ORGANISM: Artificial sequence
<220> FEATURE:
<223> OTHER INFORMATION: P16 reverse

<400> SEQUENCE: 54
ccaagcacct aacaggcatc                                               20

<210> SEQ ID NO 55
<211> LENGTH: 18
<212> TYPE: DNA
<213> ORGANISM: Artificial sequence
<220> FEATURE:
<223> OTHER INFORMATION: P17 forward

<400> SEQUENCE: 55
ccgaaacatg gatttggc                                                 18

<210> SEQ ID NO 56
<211> LENGTH: 18
<212> TYPE: DNA
<213> ORGANISM: Artificial sequence
<220> FEATURE:
<223> OTHER INFORMATION: P17 reverse

<400> SEQUENCE: 56
tcaaccggca aagtcagc                                                 18

<210> SEQ ID NO 57
<211> LENGTH: 18
<212> TYPE: DNA
<213> ORGANISM: Artificial sequence
<220> FEATURE:
<223> OTHER INFORMATION: G1 forward

<400> SEQUENCE: 57
gacagctccc cacacacc                                                 18
```

```
<210> SEQ ID NO 58
<211> LENGTH: 18
<212> TYPE: DNA
<213> ORGANISM: Artificial sequence
<220> FEATURE:
<223> OTHER INFORMATION: G1 reverse

<400> SEQUENCE: 58
ttcctgcctg agctgacc                                                 18

<210> SEQ ID NO 59
<211> LENGTH: 18
<212> TYPE: DNA
<213> ORGANISM: Artificial sequence
<220> FEATURE:
<223> OTHER INFORMATION: G2 forward

<400> SEQUENCE: 59
tgcctctctt gctctggg                                                 18

<210> SEQ ID NO 60
<211> LENGTH: 18
<212> TYPE: DNA
<213> ORGANISM: Artificial sequence
<220> FEATURE:
<223> OTHER INFORMATION: G2 reverse

<400> SEQUENCE: 60
gtgggcatgg gtcagaag                                                 18

<210> SEQ ID NO 61
<211> LENGTH: 18
<212> TYPE: DNA
<213> ORGANISM: Artificial sequence
<220> FEATURE:
<223> OTHER INFORMATION: G3 forward

<400> SEQUENCE: 61
acagctgccc acttctgg                                                 18

<210> SEQ ID NO 62
<211> LENGTH: 18
<212> TYPE: DNA
<213> ORGANISM: Artificial sequence
<220> FEATURE:
<223> OTHER INFORMATION: G3 reverse

<400> SEQUENCE: 62
gcgaggacca aactcagg                                                 18

<210> SEQ ID NO 63
<211> LENGTH: 18
<212> TYPE: DNA
<213> ORGANISM: Artificial sequence
<220> FEATURE:
<223> OTHER INFORMATION: G4 forward

<400> SEQUENCE: 63
attcaggcgc tttgcatc                                                 18

<210> SEQ ID NO 64
<211> LENGTH: 18
<212> TYPE: DNA
<213> ORGANISM: Artificial sequence
<220> FEATURE:
<223> OTHER INFORMATION: G4 reverse

<400> SEQUENCE: 64
```
aggctggtca catgggtg					18

<210> SEQ ID NO 65
<211> LENGTH: 18
<212> TYPE: DNA
<213> ORGANISM: Artificial sequence
<220> FEATURE:
<223> OTHER INFORMATION: G5 forward

<400> SEQUENCE: 65
catggtcttg gactgggc					18

<210> SEQ ID NO 66
<211> LENGTH: 18
<212> TYPE: DNA
<213> ORGANISM: Artificial sequence
<220> FEATURE:
<223> OTHER INFORMATION: G5 reverse

<400> SEQUENCE: 66
agctcgatct tcatgcgg					18

<210> SEQ ID NO 67
<211> LENGTH: 20
<212> TYPE: DNA
<213> ORGANISM: Artificial sequence
<220> FEATURE:
<223> OTHER INFORMATION: Alu 1 forward

<400> SEQUENCE: 67
gcgcggtggc tcacgcctgt					20

<210> SEQ ID NO 68
<211> LENGTH: 20
<212> TYPE: DNA
<213> ORGANISM: Artificial sequence
<220> FEATURE:
<223> OTHER INFORMATION: Alu 1 reverse

<400> SEQUENCE: 68
cctcccaaag tgctgggatt					20

<210> SEQ ID NO 69
<211> LENGTH: 20
<212> TYPE: DNA
<213> ORGANISM: Artificial sequence
<220> FEATURE:
<223> OTHER INFORMATION: Alu 2 forward

<400> SEQUENCE: 69
cgccactgca ctccagcctg					20

<210> SEQ ID NO 70
<211> LENGTH: 20
<212> TYPE: DNA
<213> ORGANISM: Artificial sequence
<220> FEATURE:
<223> OTHER INFORMATION: Alu 2 reverse

<400> SEQUENCE: 70
cgatctcctg acctcatgat					20

PROBES FOR SPECIFIC ANALYSIS OF NUCLEIC ACIDS

CROSS REFERENCE TO RELATED APPLICATIONS

This is a national stage application based on PCT/Ep2010/060715, filed on Jul. 23, 2010, which claims priority to British Patent Application No. GB0912909.9, filed on Jul. 23, 2009. This application claims the priority of these prior applications and incorporates their disclosures by reference in their entireties.

The present invention relates to a method for detecting or enriching target nucleic acids in a complex nucleic acid sample. In such a method the sample is fragmented and fragments containing the target nucleic acid are covalently attached, at or near one end by nucleic acid ligation ("single-sided ligation", i.e. one end of the target fragment is not involved in the ligation reaction and remains free), to a single target-specific probe per target fragment. Optionally, common nucleic acid adaptors may be non-target-specifically added to said free end of the fragments. The probes may contain elements facilitating enrichment of the target fragments, such as by purification (e.g., by immobilisation to a solid phase), or amplification (e.g., by utilising elements in the probes and optional adaptors). In this way, target nucleic acids may be obtained from complex samples for subsequent analysis by, e.g., nucleic acid sequencing, microarray, qPCR, visualisable hybridisation probes, in situ analyses, etc. The feature of the present invention of providing (and using) a ligation probe specific for only one end of a target nucleic acid (or target nucleic acid fragment) is advantageous, and facilitates particular applications not possible with known methods.

It is often desired to isolate large numbers of sub-genomic sequences to allow their further characterisation, e.g. the isolation of the genomic regions believed to be of relevance to a particular physiological or pathological condition. This is particularly so following the advent of parallel methods of high-throughput sequencing, which necessitate methods for rapidly isolating genomic sequences of interest for use in such sequencing methods.

One known method for amplifying (amplification constituting a means of "enriching" according to the present invention) in parallel a plurality of target nucleic acids from a sample of nucleic acids is disclosed in WO 2005/111236. In this method, partially double-stranded "Selector" nucleic acid molecules (either a single symmetrical molecule in which the longer strand overhangs at both ends, or two asymmetrical molecules each having a single-stranded overhang at only one end) are hybridised via their single-stranded overhangs in a target-specific manner to both ends of single-stranded (denatured) target fragments resulting from fragmentation of the nucleic acid sample (in the case of the single symmetrical Selector, the hybridised Selector-target fragment becomes circularised). In a particular embodiment of the method using the symmetrical Selector, only one end of the target fragment hybridises to an end of the Selector, the other end of the Selector hybridising internally of the target nucleic acid fragment and requiring a structure-specific endonuclease to resolve the resulting structure by cleaving off the portion of the target fragment "protruding" beyond the internal hybridised region. In all cases, therefore, the amplifiable portion of the target fragment is delineated by the regions (whether both end regions or one end and one internal region) of known sequence to which the Selector(s) has been designed to hybridise. Following hybridisation (and, where appropriate, resolution of the secondary structure) the Selector(s) and target nucleic acid fragment are joined by ligation to give (i) in the case of the symmetrical Selector, a circular nucleic acid molecule and (ii) in the case of the asymmetrical Selectors a linear molecule comprising the target fragment flanked by Selectors. The double-stranded region of the Selector(s) contains a primer pair motif which is common to the plurality of different target-specific Selectors used in a multiplex assay. Hence, amplification of multiple target fragments can be achieved simultaneously whilst avoiding amplification artefacts which can result from the use of multiple, different primer pairs.

In the method of WO 2005/111236, two target-specific hybridisation events are required for each target fragment; hybridisation of Selector(s) to both ends, or to one end and one internal sequence, of the target fragment. This inevitably requires knowledge of the sequence of the target nucleic acid at least at these two hybridising regions, in order for target-specific hybridisation probes to be designed.

However, it is often desired to isolate or enrich for genomic sequences or fragments based on knowledge of only one region of sequence, i.e. wherein the fragment (or region of sequence) it is desired to isolate is not bounded at both ends (delineated) by regions of known sequence. This will frequently be the case when the need to isolate the target sequence (e.g. fragment) arises from a desire to subject the sequence/fragment to sequencing, i.e. at least part of the sequence is not known. A particular example of this is the analysis of chromosomal translocation breakpoints, where it is desired to determine the precise sequence of the region of a chromosome to which a region of another chromosome, containing known sequence, has become fused. Other examples include the analysis of splicing patterns or VDJ recombination events. Hence, there is a need for a method of rapidly and efficiently detecting (or enriching for or capturing) one or a plurality of target nucleic acids which does not require knowledge of the sequence of regions at both ends of the corresponding target nucleic acid fragment.

It has now been found that the limitation of the above-described Selector(s) method may be overcome through the use of a single (i.e. a single species of) probe, that is a single (or single species of) probe per target nucleic acid, which has specificity to a region of known sequence in the nucleic acid fragment corresponding to the target nucleic acid. In other words, the present invention is based on the novel feature of using only one target-specific probe for each target nucleic acid, which binds in a target-specific manner only once (more particularly at only one site) in the target nucleic acid fragment. Thus, for each target nucleic acid fragment resulting from fragmentation of the nucleic acid sample, only one target-specific hybridisation and ligation ("binding") event occurs; the target-specific ligation is single-sided with respect to the target nucleic acid fragment and therefore only a single region of known sequence in the target nucleic acid fragment is required in order to design the probe. In other words, there need only be, and is only, one defined binding site for the probe in each target nucleic acid fragment, i.e. the sequence of the target fragment needs to be defined at only one site, e.g. at only one end. The method of the invention thereby enables and, advantageously, facilitates the detection or enrichment of genomic nucleic acids lacking known sequence at both ends (i.e. having known sequence at only one end).

The use of such a single target-specific probe offers further advantages beyond the ability to detect or enrich for target nucleic acids having unknown sequence at one end (i.e. the end other than that to which the target-specific probe hybridises). The ligation of the probe to the target nucleic acid fragment results in a covalent connection between these molecules. Thus, the actual genomic fragment, and not an amplification product thereof, becomes covalently connected to the probe. In certain embodiments of the invention the probe contains elements facilitating immobilisation of the probe to a solid phase. In such embodiments the covalent connection between the target nucleic acid fragment and the probe results in a stable capture of the former and allows the use of highly stringent washing steps to remove non-specifically hybridised (non-ligated) fragments, resulting in a high specificity. Washes of such high stringency cannot be used with known hybridisation—(as opposed to ligation—) based methods such as microarray capture and fluorescence in situ hybridisation (FISH), and the ability to use such washes in the present method is therefore advantageous.

The use of the single target-specific probes in the methods of the invention need not be limited only to methods using genomic DNA. In view of the favourable results obtained using human genomic DNA (see the Examples) it is envisaged that the methods of the invention would work equally well with any DNA sample that contains one or more target nucleic acids. Thus, for example, the methods of the invention could use one or more cDNA samples, e.g. cDNA obtained, derived or synthesised from the RNA of whole organisms, specific tissues, cell types etc or biological samples exposed to various conditions which may alter the gene expression of said sample resulting in an altered cDNA population.

Accordingly, the present invention provides a method for detecting or enriching for a target deoxyribonucleic acid (DNA) present in a nucleic acid sample, said method comprising:

(a) fragmenting a nucleic acid sample to generate nucleic acid fragments including a target fragment containing said target DNA;

(b) rendering said fragments, including said target fragment, at least partially single-stranded, wherein the single-stranded portion includes an end portion and wherein the length of said single-stranded portion is sufficient to allow hybridisation of at least part of the single-stranded portion of said target fragment to the probe of step (c);

(c) contacting the at least partially single-stranded fragments of step (b) with oligonucleotides A and B of a single target-specific nucleic acid probe, wherein:

(i) oligonucleotide A is a single-stranded oligonucleotide comprising at one end a first target-specific part comprising at least 10 nucleotides complementary in sequence to at least part of said single-stranded portion of said target fragment, and comprising at the other end a second non-target-specific part which comprises a nucleotide sequence complementary to at least a portion, including one end, of oligonucleotide B of the probe, and (ii) oligonucleotide B is a single-stranded oligonucleotide which may contain or carry at least one element for detection and/or enrichment (in particular detection, amplification and/or capture) of said target fragment, and of which at least a portion, including one end, is complementary in sequence to the second non-target-specific part of oligonucleotide A, such that said target fragment becomes annealed to said probe through hybridisation to the first target-specific part of oligonucleotide A resulting in only one target-specific probe-binding event per target fragment;

(d) directly or indirectly ligating oligonucleotide B of said probe to the part of the single-stranded portion of said target fragment which is hybridised to oligonucleotide A of said probe to produce a probe-target fragment hybrid; and (e) detecting or enriching for said probe-target fragment hybrid.

As described in more detail below, the method of the invention may advantageously include an additional step, between steps (a) and (b) in which a common nucleic acid adaptor is non-target-specifically annealed to the ends of the fragments. Such a method involving the use of a common adaptor represents a preferred embodiment of the present invention. In particular, in such a step the annealed adaptor becomes ligated to the fragments only at the 3' ends or only at the 5' ends of the strands of the fragments. More particularly, the adaptor is ligated to one end of the strand of the target fragment to which, at the other end, oligonucleotide B of the probe is ligated in step (d). In other words, in the target fragment the adaptor is ligated at the opposite end of the strand to which the target-specific probe becomes ligated.

The method of the invention may be performed as described above ("simplex" format) to enrich for a single (i.e. a single species of, which will normally be present in many copies) target fragment or for a plurality of target fragments which are sufficiently similar in sequence so as to be possible to enrich for using the same probe. In this context it will be seen that the term "single" as used in relation to the target-specific probe in part (c) means single in the context of a particular target fragment, namely that one probe (or more particularly one type or species of probe) is used for each target fragment (i.e. a single probe per target fragment). Thus, where there is only one target fragment only one probe (in the sense of one species of probe) will be used. Accordingly, part (c) above may alternatively be expressed as:

"(c) contacting the at least partially single-stranded fragments of (b) with oligonucleotides A and B of a target-specific nucleic acid probe wherein for each target fragment a single probe is used, wherein"

It is clear from the above that "single" probe means single species of probe and does not imply any limitation on the actual number of probe molecules used.

Alternatively, a plurality (i.e. a plurality of species) of probes may be used in a "multiplex" format simultaneously to enrich for a plurality of target DNAs. Hence, in such a latter aspect the method as defined above is for enriching for a plurality of target DNAs, wherein in step (c) said target fragments are contacted with oligonucleotides A and B of a plurality of nucleic acid probes, each having an oligonucleotide A with a different first target-specific part, whereby a plurality of different target fragments may be annealed to said probes. In such a multiplex method, as stated above, for each target fragment of the plurality (i.e. each different type or species of target fragment) a single (i.e. in the sense of a single species of) probe will be used. Thus, a plurality of probes will be used, with a (different) single probe for each target fragment. The term "plurality" as used herein means 2 or more (or at least 2), more particularly 3 or more (or at least 3), or 4, 5, 6, 8, 10, 15, 20, 30, 50, 70 or 100 or more etc. In certain embodiments even higher numbers of probes may be used and very many different targets may be enriched or detected, e.g. 500, 1000, 2000, 5000 or 10,000 or more. For example, 10, 100, 1000 or 10000 different probes may simultaneously be used to detect or enrich for, respectively, 10, 100, 1000 or 10000 different target fragments.

The term "enriching" as used herein is used broadly and includes any means of selecting, isolating and/or capturing a DNA sequence of interest ("target DNA") from a nucleic acid sample which contains other nucleic acids, particularly other DNAs, in addition to (and including DNAs being part of the same DNA molecule as) the target DNA. Thus "enriching" encompasses any means of practically, if not necessarily physically, "separating" the target DNA from the other nucleic acids present in the sample, more particularly by means of covalently attaching a probe thereto in order that the target DNA may be subjected to analytical and/or preparative or synthetic, or other enrichment, techniques. "Enriching" for the target DNA as used herein may, for example, be amplification by one of the many known methods of nucleic acid amplification, or may be physical capture, for example by immobilisation to a solid phase, optionally followed by amplification.

Although as discussed further below, in certain embodiments the method may involve immobilisation on a solid phase, this is not a necessary feature of the method. Thus, the method may be carried out in solution, i.e. may be a homogeneous method.

The term "detecting" is also used broadly herein and includes any means of detecting or determining or assaying for the presence of the target DNA, or any means of analysing the target DNA. Direct analysis of the target DNA sequence (i.e. sequencing of all or any part of the target DNA) is encompassed by the term detecting. As described further below this may be accomplished by any means enabled by the probe ligated to the target molecule, such as the presence in the probe of a sequencing primer binding site Thus, the method of the invention allows a selected target fragment to be sequenced. More particularly, a target fragment selected by means of the target-specific probe according to the present invention may be directly sequenced. Of course, the invention also covers indirect analysis, e.g. sequencing, of the target DNA, for example analysis, e.g. sequencing, of an amplified target DNA, or of a captured target DNA fragment.

The step of detecting or enriching for the target DNA involves detecting or enriching for the probe-target fragment hybrid. Thus, detection or enrichment of the target DNA may be achieved by any means of detection or enrichment which is selective for the hybrid. As described in more detail below, this may be achieved by means of detection and/or enrichment (e.g. capture and/or amplification) elements which are present in the probe (and thereby incorporated into the hybrid, but not present on other, non-target, fragments present in the sample which have not become ligated to the probe) or more generally by any means which is dependent on the ligation of the probe to the target fragment or, put another way, dependent on formation of the probe-target fragment hybrid.

The term "target DNA" as used herein means a DNA of interest which it is desired to detect or for which it is desired to enrich. This will generally be a part (or a portion or segment) of a longer DNA molecule which may be present in the sample. Thus, it may be a region or stretch of a longer DNA present in the nucleic acid sample (or more particularly, DNA sample). The target DNA may be of any length, but in order to be detected or enriched by the method of the invention must comprise or be contained within a fragment (the "target fragment") produced by the step of fragmenting the nucleic acid sample. The sequence of the target DNA may not be known, providing that at least a portion of the target fragment is of known sequence in order to facilitate the design of the probe, which must be able to hybridise to a single region of the target fragment.

Whilst the target DNA may be of any length, advantageously the methods disclosed herein may be used for detecting or enriching large target fragments or, alternatively viewed, target fragment polynucleotides of a minimum length, by which is meant target fragments comprising at least 30 nucleotides. More preferably, the target fragments comprise at least 40, 50, 60, 70, 80, 90, 100, 125, 150, 200, 250 or 300 nucleotides. Where the target fragment comprises an overhang, e.g. as a result of cleavage (fragmentation), the minimum length of the target may include or exclude the overhang sequence.

The "nucleic acid sample" referred to above may be any sample which contains any amount of nucleic acid, from any source or of any origin, in or from which it is desired to detect or enrich a target DNA known or suspected to be comprised therein. More particularly, the sample may be any sample that contains DNA. The sample may be complex, e.g. whole genomic DNA, cDNA from a whole organism, tissue or cell population, or a fraction thereof. In this regard it may for example be a direct product of a nucleic acid isolation procedure, or of a cell lysis procedure, or it may be further be fractionated or purified in some way, e.g. it may contain nucleic acids which have been partially or fully separated in some way, or treated in any way, e.g. RNA treated to produce cDNA. The sample may be from any eukaryotic or prokaryotic or viral source, e.g. may be of microbial (for example bacterial or fungal), plant, or animal (e.g. vertebrate, mammalian or primate) origin. In a particular aspect, the sample may be of human origin e.g. human genomic DNA or cDNA. The sample may be from a single origin, or may be formed from a pooling of a plurality of samples from different origins. In the latter case, the fragmenting step (a), and optionally one or more further steps of the method, may be performed on the samples separately prior to said pooling. For example, said nucleic acid sample may represent the pooling of a number of patient samples, such that the method of the invention allows parallel enrichment of target DNAs from multiple patients.

Thus, the target DNA is preferably genomic DNA. It may represent total genomic DNA or it may be a sub-fraction thereof. Thus, the sample may comprise or may be derived from genomic DNA, e.g. by separating/isolating genomic DNA directly or copying (e.g. amplifying) genomic DNA.

Alternatively, the target DNA is preferably cDNA (complementary or copy DNA). The, the sample may comprise cDNA or a subfraction thereof, wherein cDNA is DNA that is complementary to messenger RNA or DNA that has been synthesized from messenger RNA by reverse transcriptase. Preferably, in the context of the present invention the cDNA has been treated to comprise double stranded DNA. Thus cDNA can be considered to be a copy of the RNA present in a cell at the time of extraction or isolation or a fraction thereof, i.e. it represents all or some of the genes that were expressed in said cell at the time of isolation. Hence, a cDNA sample may represent the genes expressed from a whole organism or a part thereof, e.g. a tissue or cell type or group or sub-group thereof, and may further represent genes expressed under specific conditions, e.g. at a particular time, in a specific environment, at a stage of development or in response to stimulus etc. The cDNA may represent a subfraction of the RNA isolated from any of the above sources, e.g. the RNA or cDNA may be fractionated, e.g. by size, to encompass only a proportion of the genes expressed in the source. The cDNA may be derived from a single source or multiple sources as described elsewhere herein. The sample may comprise cDNA derived directly from the mRNA or the cDNA may be derived indirectly, e.g. the cDNA may be amplified, e.g. via the production of a cDNA library.

In a first step (a) of the method the nucleic acid sample known or suspected to contain the target DNA is fragmented to produce fragments, amongst which will exist (if the target DNA is present in the sample, and if the method of fragmentation is selected appropriately) at least one (i.e. at least one species of) fragment containing the target DNA. The term "fragmenting" is used broadly herein to include any means by which the nucleic acid in the sample may be fragmented or cleaved (i.e. divided or "cut" into smaller pieces or fragments). Thus, fragmentation may be carried out enzymatically, e.g. using restriction or other endonucleases or nucleases such as DNase, and/or physically, e.g. by nebulisation or sonication or any shear-based methods. Such physical methods result in unpredictable, non-sequence-specific fragmentation, as do certain (non-restriction) endonucleases. Thus both random, and pre-determined (or site-specific) fragmentation is encompassed, but the latter is preferred. Accordingly, fragmentation using an enzyme which cleaves at a known or defined site is preferred, in other words enzymes which cleave sequence-specifically or structure-specifically, or, put another way, which cleave to generate ends of known (defined) sequence, for example restriction endonucleases and FLAP endonucleases. However, also encompassed by the reference to "fragmenting" in step (a) is fragmentation of a nucleic acid sample which inherently may occur as a result of the age of a sample, the conditions in which it is stored and any treatment of the sample (e.g. fixation, for example in a tissue sample), and the degradation to which these factors contribute. Any suitable class of restriction endonuclease may be used, including type II and type IIs enzymes. The use of type IIs endonucleases is particularly advantageous as these result in fragments which will not have the same end sequences, thereby improving the chances targeting the probe to the intended target fragment through the use of an oligonucleotide A of appropriate sequence. Alternatively, the cleaving (fragmenting) may be achieved using a flap endonuclease, wherein an added nucleic acid or oligonucleotide is only partially hybridisable, due to being partially double-stranded, to a sequence in the nucleic acid sample resulting in a protruding non-hybridised region of the nucleic acid sample adjacent to a hybridised region. This secondary structure is the substrate for a so-called structure-specific "flap endonuclease" enzyme which cleaves the nucleic acid sample at the junction of the hybridised and non-hybridised regions (Lyamichev V et al, Science. 1993 May 7; 260(5109):778-83). The use of a flap endonuclease may be advantageous in the absence of a (known) restriction enzyme recognition sequence near to the target DNA within the nucleic acid sample, as it allows cleavage (fragmentation) to be targeted at any region of known sequence. Flexibility in positioning the site of cleavage is thereby afforded. When using a flap endonuclease, a preceding physical fragmentation step may be desirable.

Fragmenting means may be used in combination, e.g. the use together of two or more endonucleases, more particularly two or more restriction endonucleases, or the use together of an enzymatic and a physical means. Furthermore, the nucleic acid sample may be differently fragmented in separate aliquots, which aliquots are then pooled and together subjected to the remaining steps of the method of the invention.

Hence, the fragmenting may be achieved by separating the nucleic acid sample into a plurality of aliquots and fragmenting the respective aliquots with different means or different combinations of means, such means being for example restriction enzymes. The aliquots are then subjected to the remaining steps of the method and may be pooled at any point during the method, for example before step (b), before step (c), before step (d) or before or after step (e) to give the (single) nucleic acid sample referred to in the above method. Such an embodiment should be distinguished from the separate fragmenting and subsequent pooling discussed above, in which case the samples are of different origins (rather than aliquots of a single sample). However, in that aspect the samples of different origin may themselves respectively be fragmented in multiple separate aliquots and respectively pooled as mentioned above, before the pooling to give the (single) nucleic acid sample, referred to in the above method, for use in subsequent steps of the method.

Known heterozygous polymorphisms in the sample nucleic acid may be exploited by fragmenting the sample using, if possible, endonucleases which recognise a sequence inactivated in at least one instance by such a polymorphism. By designing probes targeted to the fragments produced in the presence and absence of cleaving at the polymorphic endonuclease recognition site said haplotype-specific fragments may independently be enriched and analysed.

After the fragmenting step the fragments of the nucleic acid sample, including the fragment which contains the target DNA, are rendered at least partially single-stranded (step (b)). Where the fragments are not made completely single-stranded, they will at least be single-stranded at an "end portion", which means that the part of such fragments which is single-stranded will include one end of the fragments, and the single-stranded portion will be of sufficient length to allow, in the case of the target fragment, hybridisation of at least part of said portion to the probe. Thus "rendering at least partially single-stranded" as used herein encompasses all means of causing a double-stranded DNA fragment to become single-stranded wholly or at least at an end-containing portion. Such means include denaturation, e.g. by heat or pH or through the use of chemicals, as is known in the art. Heat denaturation is particularly preferred. Rendering the fragments only partially single-stranded such that they remain largely or at least partially double-stranded is advantageous, especially for the enrichment of long genomic sequences, as this avoids to some extent the undesirable cross-reactivity between single-stranded nucleic acid fragments and thereby reduces the incidence of hybrids which must be distinguished between.

Alternatively, at least partial single-strandedness can be achieved by 3' or 5' exonucleolysis using an appropriate 3' or 5' exonuclease. Starting at a free double-stranded fragment end, such enzymes progressively degrade or digest one strand of a double-stranded nucleic acid, leaving the complementary strand and rendering the nucleic acid single-stranded along the length of the enzyme's action. The extent of exonucleolytic degradation (i.e. the length of the resulting single-stranded region) may be controlled by the duration of the reaction. The duration of the exonuclease reaction is chosen in order that an appropriate length of one end of the strands of the fragments is removed. The extent of digestion must be sufficient to allow a productive hybridisation (i.e. hybridisation capable of templating ligation) with the first target-specific part of oligonucleotide A of the probe, but not so much that the fragment loses all double-strandedness and becomes two single-stranded fragments. Suitable exonucleases are known in the art and include e.g. exonuclease III (3') and lambda exonuclease (5'). The use of exonuclease III is particularly preferred. As regards the use of exonucleases it should be noted that, if fragmentation is to be performed in step (a) by restriction endonucleolysis, it must be borne in mind when selecting the endonucleases whether they produce 5' or 3' overhanging, or blunt, ends, as certain types of restriction ends are poor substrates for certain exonucleases. The substrate preferences of exonucleases are known in the art. For example, exonuclease III does not favour 3' overhanging ends, and hence the use of endonucleases which leave 5' overhanging ends is in some aspects preferred. As mentioned above, the single-stranded end-containing portion of the target fragment must be able to hybridise, at least in part, to the probe. Thus, the single-stranded portions of the fragments must be of sufficient length to support, in step (c), stable base-pairing between at least part of the single-stranded portion of the target fragment and the first target-specific part of oligonucleotide A of the probe. "Sufficient to allow hybridisation" as used herein therefore means that the partially single-stranded target fragment must be single-stranded to the extent necessary to permit a productive hybridisation with the probe, i.e. a hybridisation capable of templating ligation of the hybridised portion of the fragment to oligonucleotide B of the probe in step (d). This does not require, but does include, 100% complementarity between the first target-specific part of oligonucleotide A of the probe and the corresponding region of the single-stranded portion of the target fragment. "Complementary", as used herein, means functionally complementary, i.e. a level of complementarity sufficient to mediate hybridisation, which encompasses degrees of complementarity less than 100%.

The reference in step (b) above to "at least part" of the single-stranded portion of the target fragment encompasses, for instances where said single-stranded portion is longer than the first target-specific part of oligonucleotide A of the probe to which at least part of said single-stranded portion is complementary, hybridisation of said part of oligonucleotide A to a portion of said single-stranded portion which includes the end of the target fragment as well as, in the alternative, to an internal non-end portion. Thus, the first target-specific part of oligonucleotide A has functional complementarity, and therefore hybridises, either to an end-containing portion or to an internal non-end-containing portion of the single-stranded portion which, as mentioned above, includes an end portion. Thus, in certain embodiments of the invention the first target-specific part of oligonucleotide A hybridises at (is functionally complementary to) one end of the single-stranded portion of the target fragment. As discussed in more detail below, in certain other embodiments of the invention the hybridisation and ligation steps (c) and (d) occur through resolution of a generated secondary structure using a flap endonuclease (as discussed above in the context of fragmenting step (a)), the substrate for which is generated by hybridisation of oligonucleotide A of the probe to such an internal non-end portion of the target fragment.

Once the fragments of the nucleic acid sample have been rendered at least partially single-stranded in step (b) they are contacted with oligonucleotides A and B of the single target-specific probe of step (c). As noted above, reference to a "single" probe is intended as a reference to a single species of probe; although in practice many copies of the probe (and other nucleic acid reagents) will be used, for a given particular target fragment only one probe (albeit many copies thereof), rather then two or more different probes, is contacted with the fragments of step (b). The probe comprises or consists of oligonucleotides A and B hybridised together. As oligonucleotide A has a first target-specific part which is not complementary to oligonucleotide B, the probe is partially single stranded. As is apparent from step (c), the probe may be provided "intact" (with oligonucleotides A and B pre-hybridised) or oligonucleotides A and B may be added un-hybridised in which case hybridisation to form an intact probe will occur during the step (c) of annealing the probe (oligonucleotide A) with the target fragment (as used herein, "annealed" means non-covalently joined or connected and therefore does not include ligation). Reference in step (c) to "oligonucleotides A and B of a single target-specific nucleic acid probe" also encompasses a probe wherein oligonucleotides A and B are connected together, or joined, directly or indirectly, to form a single contiguous oligonucleotide, oligonucleotides A and B representing a self-complementary portion thereof (wherein oligonucleotides A and B may be annealed (hybridised) together). Thus, in such a probe oligonucleotides A and B may represent the respective "parts" (more particularly "hybridising parts") of a single continuous partially self-complementary oligonucleotide. In such a case, the end of the probe other than the single-stranded target-specific part (of oligonucleotide A) is a hairpin or hairpin loop. Hence, as used herein, reference to "oligonucleotides" A and B is a reference to the respective parts of such an oligonucleotide. Alternatively viewed, oligonucleotides A and B may be seen as oligonucleotide sequences, which may be provided either as separate oligonucleotide molecules (i.e. separate moieties) or they may be part of a single oligonucleotide molecule. When oligonucleotides A and B are parts of such a single oligonucleotide, the oligonucleotide may be pre-hybridised or un-hybridised when contacted with the at least partially single-stranded fragments in step (c).

Advantageously, the fragments are contacted with un-hybridised oligonucleotides A and B of the probe, with a large amount of oligonucleotide A, and an even greater amount of oligonucleotide B (except in the case that oligonucleotides A and B are parts of a single oligonucleotide), being added in order that as high a proportion as possible of the target fragments are annealed thereto. The use of oligonucleotides A and B of the probe in excess, or large amounts of these probe oligonucleotides relative to the amounts of the fragments of the nucleic acid sample is, in addition to minimising the requirement for sample material, to try to ensure that a large fraction (at or close to 100%) of the available target fragments are bound to the probe, which is necessary for equal representation of the target fragments. Equal representation is important in, for example, sequencing applications, for efficient resequencing. Where oligonucleotides A and B are provided as part of a single probe, this helps to ensure that A and B oligonucleotides are hybridised together without having to add excess oligonucleotides.

The target-specific nucleic acid probe, and hence oligonucleotides A and B, are generally comprised of DNA. However, also included are probes made up of or including ribonucleotides or synthetic or modified nucleotide residues that are capable of participating in Watson-Crick type or analogous base-pair interactions. Thus, also included are probes comprised of DNA analogues or modified DNA, e.g. PNA or other derivatives including non-nucleotide backbones.

Thus, the partially double-stranded probe used in the method of the invention is comprised of two hybridised oligonucleotides, or two parts of a single, partially self-complementary oligonucleotide, A and B. Oligonucleotide A acts to template the ligation of the target fragment to oligonucleotide B and therefore comprises a first target-specific part and a second non-target-specific part. By "first target-specific part" is meant a part of oligonucleotide A of at least 10 nucleotides in length which is complementary in sequence to at least part of the single-stranded portion of the target fragment. The reference in step (c) (i) to "at one end" is meant in a general sense, i.e. that the first target-specific part and the second non-target-specific part are generally at opposite ends of oligonucleotide A, and does not require that the first target-specific part is at the very terminus of oligonucleotide A. "Complementary" as used here is as defined above, i.e. functionally complementary (capable of mediating hybridisation). Hence, "complementary" refers to said part as a whole rather than the individual nucleotides and may not necessarily mean 100% complementarity between the first target-specific part of oligonucleotide A and the part of the single-stranded portion of the target fragment to which it hybridises. However, the furthest-apart target fragment-complementary nucleotides of said part must delineate a stretch of at least 10 nucleotides. Thus, the first target-specific part may be 10 nucleotides long or of any length above 10 nucleotides such as, e.g., 10, 11, 12, 13, 14, 15, 16, 17, 18, 19, 20, 25, 30, 35, 40, 50, 100 or any integer between or above these, providing that the length is sufficient to mediate a productive hybridisation, i.e. a hybridisation sufficient to template a ligation between the target fragment and oligonucleotide B. Such a productive hybridisation does not necessarily require that the terminal nucleotides of the relevant end of oligonucleotide A are comprised within the target fragment-complementary stretch of nucleotides (first target-specific part), and therefore oligonucleotide A may contain one or more terminal nucleotides at that end which are not complementary to the target fragment.

The non-target-specific part of oligonucleotide A will typically be of at least 20 nucleotides in length in order to facilitate a stable, productive hybridisation with oligonucleotide B. If the probe is a single, partially self-complementary oligonucleotide, the intramolecular hybridisation may permit a shorter non-target-complementary region of oligonucleotide A, though in such a case the ligase required in the subsequent ligation step will require a double-stranded region of about 6-10 nucleotides. The length of the non-target-specific part of oligonucleotide A will represent the difference between the length of the target-specific part and a maximum length of oligonucleotide A of about 200 nucleotides. Preferably, the first target-specific part and the second non-target-specific part of oligonucleotide A each consist of 20, 25 or 30 or more nucleotides. Oligonucleotide A may in total be, for example, 16 to 200 nucleotides long, more particularly, 18, 20, 30, 40, 50 or 60 to 100, 120, 150 or 200. A representative length range may yet more particularly be 16, 18 or 20 to 40, 50, 60, 70, 80 or 100, or at the higher end, 30, 40 or 50 to 60, 70, 80, 90, 100, 120, 150 or 200.

Oligonucleotide B must be at least of a length sufficient to maintain a productive hybridisation with at least part of the non-target-specific part of oligonucleotide A, but as discussed below may be longer than this and may overhang oligonucleotide A at the other end of the probe from the single-stranded target-specific part. Thus typically, oligonucleotide B will be at least 20 nucleotides long, but may be less, e.g. at least 6, 8 or 10 nucleotides long in the case of a single partially self-complementary probe. More particularly, a representative oligonucleotide B may thus be 6, 8, or 10 to 20, 30, 40, 50, 70, 80, 100, 120, 150, or 180 nucleotides long.

It will be noted that a stretch of at least 10 nucleotides (representing the first, target-specific, part of oligonucleotide A) is longer than the single-stranded "sticky" overhangs produced by restriction endonucleases. Thus, as used herein "target-specific" indicates a specificity for the target fragment which is based on a stretch of at least 10 nucleotides of the fragment. This means the annealing (hybridisation) of the probe (or more particularly oligonucleotide A of the probe) to the target fragment is dependent on (or contingent on or dictated by) the sequence of the target fragment. The sticky end hybridisation of restriction fragments is not encompassed. The probe is target-specific in the sense of being selective for the target fragment, i.e. capable of hybridising to the target fragment but not to other, non-target, fragments which do not contain a region (or part) of complementarity (in the single stranded portion) to oligonucleotide A of the probe. Thus the probe (or more particularly oligonucleotide A of the probe) discriminates or distinguishes between target and non-target fragments. The person skilled in the art will readily understand that the degree of specificity of the probe for the target fragment may be increased by increasing the length of said first target-specific part. By altering the length of said first target-specific part the "uniqueness" within the nucleic acid sample of the fragment captured by the probe may be varied, and in that way highly similar sequences such as family members or homologues of the target fragment may be included within or excluded from the fragments captured using the probe. Generally, it will be desired that in practice "target-specific" means that said first target-specific part of oligonucleotide A targets a DNA which is unique (albeit possibly present in many copies; a unique species) within the nucleic acid sample. However, as discussed above, it may be desired to use a single probe to detect or enrich for more than one DNA on the basis of shared sequence and in such cases "target-specific" will not mean that the target DNA is unique within the sample. On account of only a single target-specific nucleic acid probe being contacted in step (c) with the fragments of step (b), the method involves only one target-specific probe-binding event per target fragment. More particularly there is only one target-specific probe-binding (probe-hybridisation) event per target fragment before ligation step (d). Put another way, the method does not encompass the use of two or more target-specific probes per target fragment, nor the use of a probe which binds the target fragment more than once in a target-specific manner, in other words at more than one site, and in particular before ligation step (d).

The second non-target-specific part of oligonucleotide A comprises a nucleotide sequence complementary to at least a portion, including one end, of oligonucleotide B of the probe. Hence, the end of oligonucleotide A other than the end containing the first target-specific part hybridises to at least one end of oligonucleotide B. If oligonucleotide B contains a portion non-complementary to oligonucleotide A, this is located at the distal end of oligonucleotide B relative to the first target-specific part of oligonucleotide A. The region of complementarity may be of any length and degree of complementarity capable of mediating a productive hybridisation, i.e. a hybridisation sufficient to template a ligation between oligonucleotide B and the target fragment.

As a result of the templating action of oligonucleotide A which hybridises to oligonucleotide B and the target fragment, oligonucleotide B may be ligated to the target fragment. Oligonucleotide B therefore comprises at least a portion which is complementary in sequence to the second non-target-specific part of oligonucleotide A such that together oligonucleotides A and B form a partially double-stranded nucleic acid probe comprising at one end a single-stranded target-specific part as well as a double-stranded non-target-specific part. In cases where the probe (or more particularly oligonucleotide A) hybridises to the end of the target fragment, the probe may be designed such that, upon hybridisation, oligonucleotide B is positioned immediately adjacent to the end nucleotide of the target fragment. However, as discussed further below this is not an absolute requirement. The end of the probe other than the single-stranded target-specific part may be single- or double-stranded (or a hairpin or hairpin loop, if oligonucleotides A and B are parts of a single oligonucleotide). Thus, reference in step (c) (i) and (ii) above to "at least a portion" of oligonucleotide B means that oligonucleotide B may be longer than the portion of oligonucleotide B complementary to oligonucleotide A, in which case the "overhanging" (protruding) portion non-complementary to oligonucleotide A is at the end of oligonucleotide B other than the end which becomes ligated to the target fragment. Hence, reference in step (c) (i) and (ii) to "including one end" means that the portion of oligonucleotide B which is complementary to the non-target-specific part of oligonucleotide A includes one or, if oligonucleotide B is entirely complementary to (no longer than) the non-target-specific part of oligonucleotide A, both ends of oligonucleotide B. The ligation of oligonucleotide B to a target fragment is the only target-specific probe-binding event that will occur (and more particularly, that will occur up to or before ligation step (d)) for a given target fragment in the method of the invention.

If, as discussed above, oligonucleotide B is longer than the portion of oligonucleotide B complementary to oligonucleotide A, and the overhanging portion is at the 3' end of oligonucleotide B, said 3' end could serve as a primer for rolling circle amplification of a circularised or circularisable nucleic acid molecule hybridised to said 3' end. The nucleic acid may be pre-hybridised to oligonucleotide B or may be added separately, and may be pre-circularised or circularised by ligation as a result of a ligation reaction mediated by hybridisation to oligonucleotide B. Upon addition of DNA polymerisation reagents, an RCA product will be generated from the circularised template, said product being continuous with the probe-target fragment hybrid. Preferably, the polymerase of said polymerisation reagents is phi29 polymerase. Hence, in an in situ embodiment where the target nucleic acid fragment is immobilised, the generation of an RCA product may serve to detect the target nucleic acid. The RCA product could be visualised in situ by hybridisation of fluorescently-labelled oligonucleotides, for example.

Oligonucleotide B may contain or carry an element by which the target fragment may be detected or enriched. By "contains or carries" is meant that such an element may be contained within the nucleotide sequence of the oligonucleotide, e.g. a probe or primer binding site or other nucleic acid-based affinity-binding site (for example a binding site for a hybridisation probe or for a DNA binding protein etc., which binding site may be viewed as a capture or detection element depending on the nature of the probe or affinity binding element, or a binding site for a sequencing primer, which sequencing primer binding site may be accordingly be viewed as a detection element, or for an amplification primer, which amplification primer binding site may accordingly be viewed as an amplification element), or it may be attached or conjugated or in any way linked or coupled to or associated with oligonucleotide B. For example, it may be a functional moiety (e.g. a chemical group or a molecule) which is attached etc. to the oligonucleotide, such as an immobilisation moiety or a detection moiety (e.g. a reporter or a label). An immobilisation moiety may for example be an affinity binding moiety or group, e.g. one member of an affinity binding pair (i.e. an affinity ligand), which is attached or conjugated etc. to said oligonucleotide, and is capable of binding to the other member of the affinity binding pair (i.e. its cognate binding partner) for the purposes of capture or separation, e.g. when the cognate binding partner is attached to a solid phase.

Oligonucleotide B may contain one or a plurality of such detection or enrichment (e.g. amplification and/or capture) elements.

A detection element may as noted above be a binding site contained in the oligonucleotide sequence (e.g. a binding site for a detection probe or moiety or for a primer to be used in a detection reaction, e.g. a sequencing primer) or it may be a detection moiety which is carried in any way by the oligonucleotide, e.g. a reporter group or moiety or a label, which may be directly or indirectly signal-giving. For example it may a visualisable label, such as a coloured or fluorescent or particulate label, or a moiety which contributes to or takes part in a signal-giving reaction, e.g. an affinity binding partner or ligand or a substrate or co-factor for an enzyme.

An enrichment element may be any element for the amplification and/or capture of the target fragment, or indeed for enrichment of the target fragment by any means.

As can be seen from the discussion above an "amplification element" may be any feature of, or attached to, oligonucleotide B which may be used to amplify the target fragment of the probe-target fragment hybrid. Typically it will be an amplification primer binding site. Such an amplification primer binding site may be a binding site for a primer for single-sided amplification or polymerisation runoff, e.g. using T7 RNA polymerase primer to repeatedly prime transcription resulting in amplification (Van Gelder RN et al, Proc Natl Acad Sci USA. 1990 March; 87(5):1663-7) or a rolling circle amplification primer (see further below). It may also be a binding site for one of a number or set (e.g. pair) of amplification primers, for example to allow exponential amplification, e.g. a PCR primer or a primer for a PCR-based procedure. As described further below, if more than one amplification primer is used one or more further primer binding sites may be provided to the target fragment in a separate step. The primer binding site may also be used for the binding of a sequencing primer, or a sequencing primer binding site may be located elsewhere in oligonucleotide B.

A "capture element" is any moiety carried by (e.g. attached or conjugated to etc.) oligonucleotide B, or any feature of the sequence of oligonucleotide B (e.g. a binding site), which may potentially be used selectively to attach a probe-bound target fragment (probe-target fragment hybrid) to a solid phase or support, including for example a particle such as a bead. Hence, a capture element may be viewed as an "immobilisation element". Numerous examples of such elements are known in the art and include, e.g., an affinity binding partner, e.g. biotin or a hapten, capable of binding to its binding partner, i.e. a cognate binding partner, e.g. streptavidin or avidin, or an antibody, provided on the solid phase or support. Said interaction between oligonucleotide B and a solid phase may particularly be mediated by click chemistry (Kolb HC et al, Angew Chem Int Ed Engl. 2001 Jun. 1; 40(11):2004-2021).

The solid phase may be any of the well known supports or matrices which are currently widely used or proposed for immobilisation, separation etc. These may take the form of particles (e.g. beads which may be magnetic or non-magnetic), sheets, gels, filters, membranes, fibres, capillaries, or microtitre strips, tubes, plates or wells etc. The support may be made of glass, silica, latex or a polymeric material. Suitable are materials presenting a high surface area for binding of the analyte. Such supports may have an irregular surface and may be e.g. porous or particulate e.g. particles, fibres, webs, sinters or sieves. Particulate materials e.g. beads are useful due to their greater binding capacity, particularly polymeric beads. Conveniently, a particulate solid support used according to the invention will comprise spherical beads. The size of the beads is not critical, but they may e.g. be of the order of diameter of at least 1 and preferably at least 2 µm, and have a maximum diameter of preferably not more than 10, and e.g. not more than 6 µm. Monodisperse particles, that is those which are substantially uniform in size (e.g. size having a diameter standard deviation of less than 5%) have the advantage that they provide very uniform reproducibility of reaction. Representative monodisperse polymer particles may be produced by the technique described in U.S. Pat. No. 4,336,173. However, to aid manipulation and separation, magnetic beads are advantageous. The term "magnetic" as used herein means that the support is capable of having a magnetic moment imparted to it when placed in a magnetic field, and thus is displaceable under the action of that field. In other words, a support comprising magnetic particles may readily be removed by magnetic aggregation, which provides a quick, simple and efficient way of separating the particles following the analyte binding steps. Particularly advantageous solid phases include very small particles which can efficiently contact a high proportion of the immobilisable oligonucleotide Bs. Such particles may further be useful by retarding the movement of particle-attached target fragments through a gel, allowing separation from free, non-particle-attached (non-target) fragments. Alternatively, also preferred is the use of a chromatographic matrix modified with groups that can be reacted covalently or non-covalently with groups on oligonucleotide B of the probe.

As noted above, enrichment and/or detection of the probe-target fragment hybrid can occur by any means selective for the hybrid. As described further below, in certain embodiments of the invention the probe-target fragment hybrid may be circularised. In such an embodiment enrichment for the hybrid may take place by enriching for circular molecules, e.g. by degrading any non-circular (i.e. linear) nucleic acid molecules using an exonuclease.

Oligonucleotide B may further contain a recognition sequence for a restriction endonuclease such that the partially double-stranded, intact probe formed from the hybridisation of oligonucleotides A and B is endonucleolytically cleavable. In particular, the recognition sequence may be for a rare, infrequently-cutting endonuclease. Such a cleavage site may be useful in releasing immobilised probe-target fragment hybrids from the solid phase.

Alternatively or additionally, oligonucleotide B may contain a "molecular tag", i.e. a feature which allows an oligonucleotide B used in the method of the invention as performed on a particular sample to be distinguished from an oligonucleotide B used in the method as performed on a different sample and which thereby allows identification of the sample from which a given fragment has been enriched or detected. The molecular tag may be contained in a portion of oligonucleotide B non-complementary to oligonucleotide A. The samples may, for example, correspond to patient samples. In such an embodiment a different oligonucleotide A would be needed for each target nucleic acid, whilst the oligonucleotides B would need to differ only between the method as performed on different samples.

As discussed above, the method of the invention may be performed in multiplex. In such an embodiment, the respective oligonucleotide Bs of the plurality of nucleic acid probes comprise a common sequence which is the same in each probe. Thus, in the context of oligonucleotide B of the probe, "common" refers to a sequence of oligonucleotide B, which may comprise all of oligonucleotide B, which is the same (generic) amongst the plurality of probes used in a multiplex reaction. In particular, the common sequence in each probe may comprise the detection and/or enrichment element (e.g. amplification and/or capture element), whereby the plurality of different target fragments may be amplified and/or captured together, and/or the restriction endonuclease recognition sequence. More particularly, the plurality of nucleic acid probes in a multiplex aspect of the method comprise the same oligonucleotide B.

Once the target fragment is hybridised at one end, and oligonucleotide B is hybridised at least at one end, to oligonucleotide A of the probe, the respective ends of the target fragment and oligonucleotide B may be ligated to produce a probe-target fragment hybrid. As mentioned above, and discussed further below, a target fragment "end" for ligation may be created by hybridising a probe (or oligonucleotide A of a probe) internally in the target fragment in such a manner that a substrate for a flap endonuclease is formed, and cleaving such a structure with a flap endonuclease. The probe-target fragment hybrid comprises the target fragment ligated to the probe.

Enzymes appropriate for the ligation step are known in the art and include, e.g. Tth DNA ligase, Taq DNA ligase, *Thermococcus* sp. (strain 9° N) DNA ligase (9° N™ DNA ligase, New England Biolabs), Ampligase™ (Epicentre Biotechnologies) and T4 DNA ligase. The ligation of oligonucleotide B and the target fragment may occur directly, i.e. the respective ends are immediately juxtaposed on hybridisation to oligonucleotide A, or indirectly, in which case the hybridised ends are separated by a gap. In the latter case, the gap may be filled by an added oligonucleotide complementary to the region of oligonucleotide A in the gap (i.e. a "gap" oligonucleotide), necessitating two ligation reactions, or alternatively the gap may be filled by polymerase extension of one of the ends until the extended end meets the other end, the immediately juxtaposed ends then being ligated together. Polymerases suitable to perform such a "gap-filling" reaction are known in the art.

In aspects of the method in which the fragments of the nucleic acid sample are rendered partially (incompletely) single-stranded, after the step of ligating the probe to the target fragment a polymerase optionally may be added to the reaction to repair (fill-in) any gap between the target fragment-hybridised end of oligonucleotide A of the probe and the exonucleolytically-degraded end of the corresponding strand of the target fragment. The polymerase may extend said end of oligonucleotide A or said end of the corresponding strand of the target fragment, whichever of these ends is a 3' end. The polymerase may be a strand-displacing or a non-strand-displacing polymerase. In the former case the polymerase will, after filling said gap, continue to the end of the template by displacing (and "replacing") oligonucleotide A or the corresponding strand of the target fragment as the case may be (i.e. depending on whether the polymerase is extending from the end of oligonucleotide A or from the end of the corresponding strand of the target fragment). Such strand-displacing polymerases are known in the art and include, e.g., phi29 DNA polymerase. Non-strand-displacing polymerases may also be used and are known to include, e.g., T7 DNA polymerase. Such a polymerase will stop once it has repaired the gap and encounters double-stranded nucleic acid. The extended end may then be ligated to the end of, as the case may be, oligonucleotide A of the probe or the corresponding strand of the target fragment. In this way the double-strandedness of the probe-target fragment hybrid is substantially restored. After the ligation, and optional gap-filling, steps, unbound probe may optionally be removed from the reaction by a size separation step.

As discussed above, the probe-target fragment hybrid may be detected or enriched for by any means selective for the hybrid, for example by degradation of nucleic acid other than the hybrid or by means of a detection and/or enrichment element in oligonucleotide B. As also discussed above, such an enrichment element may be a capture, or immobilisation, element, which may be any moiety attached to, or stretch of the nucleotides of, oligonucleotide B capable of interacting with an element on a solid phase or support.

By means of the capture element the probe-target fragment hybrid may be separated (enriched) from the non-target fragments for, by example, washing or gel purification. As discussed above, the covalent nature of the ligation between the probe and the target fragment permits the use of highly stringent washes effective to remove fragments which are not ligated to the probe. Such washes are not possible in known methods in which the probe and target fragment are annealed through hybridisation, and therefore the ability to use such high stringency conditions in the present method is advantageous. Alternatively, if particles are used, another option is size selection such as gel purification.

The method of the invention may be performed with a probe having an oligonucleotide B which is immobilisable, i.e. carrying or containing an immobilisation (capture) element, or which is immobilised, i.e. wherein said immobilisation element-carrying oligonucleotide B is already bound to a solid phase. In such a latter embodiment, the step of enriching constitutes washing the immobilised probe-target fragment hybrid to remove non-target fragments.

A target fragment captured, or immobilised, as described above may directly be subjected to analytical techniques such as sequencing, or may instead firstly be amplified. Alternatively, the target fragment may not be captured/immobilised but may instead simply be amplified and/or sequenced. Thus, amplification of the target fragment may be by any suitable method for amplifying nucleic acids from a single amplification primer binding site (i.e. in oligonucleotide B), such as by the use of a T7 RNA polymerase primer, as discussed above. Sequencing reactions may be primed from such an amplification primer binding site, if present, or a separate sequencing primer binding site within oligonucleotide B. As used herein, reference to sequencing the target fragment means sequencing (i.e. determining the identity thereof) at least two consecutive nucleotides in the target fragment. As described further below, amplification may also be performed by methods which involve more than one amplification primer. A binding site for such a second or further primer may be provided to the target fragment in a separate step, as described below. Such a further amplification primer binding site will not be target fragment-specific, or will not be provided to the target fragment in a target-specific manner.

It may be desirable to release the immobilised, enriched fragments from the solid phase to facilitate their analysis. This may be achieved by cleaving in the probe of the probe-target fragment hybrid by, e.g., a restriction endonuclease having a recognition site in oligonucleotide B of the probe, as discussed above. Preferably, the restriction endonuclease is a rare-cutting endonuclease. If the immobilised probe-target fragment hybrid has become single-stranded, it may be necessary to add an oligonucleotide to render the appropriate part of the probe double-stranded prior to cleaving. Released target fragments may be then be subject to analytical techniques, such as those discussed above. Such techniques may be performed directly on the released fragments, or on amplification products thereof. In the latter case, the released fragments may be inter- or intramolecularly ligated to give linear concatemers or double-stranded circular molecules. This may require modification of the ends of the released fragments, e.g. by restriction digestion and optionally enzymatic blunting using e.g. Klenow fragment of DNA polymerase I that fills in 5' overhangs by polymerase activity and degrades 3' overhangs with exonucleolytic activity, thereby converting sticky ends to blunt ends. Circular molecules may be amplified by rolling circle amplification (RCA). For sequencing, sequences within oligonucleotide B of the probe, may be used to bind sequencing primers.

Numerous variations of the general method of the invention are contemplated, several of which are described below.

After step (a) above but before step (b) an optional further step may be performed in which a common nucleic acid adaptor is non-target-specifically annealed to the ends of the fragments. In this context, "common" means that the same adaptor is annealed to all fragments (or to a number of fragments—see further below—but in any case to more fragments than solely the target fragment(s)) within a given sample and is therefore common, or generic, to the fragments, or to a sub-population of fragments, of that sample, in contrast to the probe which anneals only to the target fragment. In cases where more than one enzyme, e.g. restriction endonucleases, have been used to fragment the sample, more than one "species" of adaptor may be used, wherein such adaptors are identical except for one "annealing end" in each case which differs to "match" the differing fragment ends produced by the enzymes.

The nucleic acid adaptors of the invention are substantially double-stranded molecules. However, by "double-stranded" in the present context does not mean (but does encompass) that said ends are "blunt", and "sticky" ends consisting of a single-stranded overhang of 1, 2, 3, 4, 5 or 6 etc. nucleotides generated by restriction enzyme digestion are included in this meaning. The adaptors may be of any suitable length.

By "non-target-specifically" is meant that said adaptor is annealed by a means which has no specificity for the target fragment in the sense of "target-specific" as defined elsewhere herein. In other words the adaptor is not selective for the target, or for non-target fragments, i.e. it does not discriminate or distinguish between target or non-target fragments. Thus, the binding (hybridisation) of the adaptor is not dependent or contingent upon a nucleotide sequence which is particular to (or specific for) the target fragment relative to the non-target fragments. As a result, such an adaptor is annealed to the ends of all of the fragments (including the target fragment). This is unlike the annealing of the probe of step (c) which is targeted to the target fragment by virtue of the complementary sequence of prescribed length present in oligonucleotide A of the probe. Such non-target specific annealing may be achieved by any method which facilitates the annealing of the adaptor to all of the fragments, such as through annealing with sticky restriction ends (if present) of the fragments, or blunt- or artificially-created sticky-end annealing. Hence, the adaptors must be designed with at least one end suitable for such annealing. For example, sticky ends of the fragments may be blunted by the use of a suitable polymerase, and single adenosines added as 3' overhangs, again through the action of an appropriate polymerase. Examples of suitable polymerases for either purpose are known in the art and include, in the former case, T4 DNA polymerase, and in the latter case Taq polymerase. If the adaptor is designed with a 5' thymidine overhang, the adenosine and thymidine overhangs will act as complementary sticky ends susceptible to ligation (known as "TA ligation"), promoting ligation of adaptors to fragments. The adaptors may be modified at one end to reduce or prevent ligation of adaptors with each other by any means which prevent ligation but do not otherwise interfere with the assay. Such modifications include the absence of 5' phosphate or 3'OH groups, addition of fluorophores or affinity groups, and the introduction of "blocking" groups such as amine groups.

Importantly, whilst said adaptor may become annealed to both ends of the fragments, it becomes ligated only at the 3' ends, or only at the 5' ends, of the strands of the fragments (thus, "annealed" is meant as defined above, i.e. it does not include ligation). This is in order that it can be ensured that, for the target fragment, an adaptor is ligated to the same strand to which oligonucleotide B will become ligated in step (d), but at the other end of that strand. Selective ligation of the adaptor to only the 3' ends, or only the 5' ends, of the strands of the fragments may be achieved by any suitable means. For example, ligation of the annealed adaptor to either the 3' or 5' ends of the strands may be controlled by dephosphorylation of the fragments or the adaptors, respectively. Suitable dephosphorylases (phosphatases) are known in the art and include, e.g., Antarctic phosphatase (New England Biolabs), shrimp alkaline phosphatase and calf intestinal phosphatase. Ligation of the fragments and adaptors may be achieved using suitable ligases as known in the art, such as T4 DNA ligase. The addition of single adenosines as 3' overhangs to the blunted fragments, and/or dephosphorylating said fragments, is also beneficial in reducing or avoiding inter-fragment ligation.

In one embodiment, therefore, the method of the invention further comprises, between steps (a) and (b), the step of non-target-specifically annealing to the ends of said fragments a common (or generic) nucleic acid adaptor, wherein the annealed adaptor becomes ligated to the fragments only at the 3' ends, or only at the 5' ends, of the strands of the fragments. As mentioned above, a single species of adaptor may be used, or one or more adaptors may be used, depending on the fragmentation procedure. Thus, the adaptor is annealed such that an adaptor is ligated to one end of the strand of the target fragment to which, at the other end, oligonucleotide B of the probe is ligated in step (d). In other words, in the target fragment the adaptor is ligated at the opposite end of the strand to which the target-specific probe becomes ligated.

In a further embodiment, the ends of the fragments are rendered sticky with respect to at least one end of the adaptor prior to ligation. In a still further aspect, dephosphorylation of the fragments or the adaptor is used to facilitate ligation of the adaptor to, respectively, either the 3' ends or the 5' ends of the strands of the fragments.

In embodiments of the method of the invention in which the adaptor-ligated target fragments are rendered completely single-stranded in step (b), the method must be designed so that the specificity of the subsequently-contacted probe is for a part of the target fragment which results in ligation of oligonucleotide B of the probe to the other end of the target fragment relative to the end to which the adaptor is ligated. Hence in such an aspect, the first target-specific part of oligonucleotide A comprises at least 10 nucleotides complementary in sequence to a portion at the end of said single-stranded target fragment other than the end to which the common nucleic acid adaptor is ligated.

The adaptor, which if used in the method of the invention will become comprised in the probe-target fragment hybrid, may contain an element (advantageously a sequence) useful for the enrichment and/or detection of the target nucleic acid. In particular, such an element or sequence will be used in conjunction with an element present in the probe. It will thus be appreciated that such an element may be a binding site for one of an amplification primer pair (or number or set of primers), the binding site(s) for the other(s) of which are provided in the probe. Accordingly, in one embodiment, the common nucleic acid adaptor comprises an element for amplification, preferably an amplification primer binding site. For example, the adaptor may comprise an amplification primer binding site orientated appropriately with respect to another such binding site in the probe such that an amplification product may be generated when the target fragment is ligated to both the probe and the adaptor. Such amplification may be by, e.g., the polymerase chain reaction (PCR), of which many modified versions (e.g. "real-time" or quantitative PCR) are well known in the art, or other amplification methods. The amplification product may be analysed by, e.g., massive parallel sequencing platforms (e.g. SOLiD (Applied Biosystems, Inc.), Illumina Genome Analyzer (Illumina, Inc.), Genome Sequencer (454 Life Sciences)) microarrays or hybridisation-based sequencing.

Said amplification primer binding site, or a separate sequence located elsewhere in the adaptor, may be used as a binding site for a sequencing primer for sequencing the enriched target nucleic acid.

Additionally or alternatively to the presence of an amplification element, the common nucleic acid adaptor may carry a molecular tag. By "molecular tag" is meant a feature which can be used to differentiate between otherwise identical adaptors. Put another way, such a tag is an element which may be used to generate distinguishable variants of a single adaptor. The tag may be a particular stretch of the adaptor's nucleotide sequence.

As discussed above, the nucleic acid sample on which the method of the invention is performed may be comprised of a plurality of pooled nucleic acid samples of different origins. Such pooling to give a single nucleic acid sample may occur after fragmenting step (a). In such an aspect, adaptors carrying different molecular tags may be ligated to the fragments of the respective nucleic acid samples prior to pooling, such that in the pooled nucleic acid sample subjected to the remaining steps of the method the fragments originating from different samples will be ligated to adaptors distinguishable by virtue of the different molecular tags. This is highly advantageous as it allows the simultaneous (parallel) analysis, in a simplex (one probe, for one or a plurality of sufficiently similar target nucleic acids) or multiplex (a plurality of probes, for a plurality of target nucleic acids) format, of multiple samples. For example, one or more target nucleic acids may be detected or enriched for in a single assay, from a plurality of differently-tagged patient samples. The use of molecularly-tagged common nucleic acid adaptors to identify the fragments of the respective samples, instead of incorporating tags in the target-specific probes, vastly reduces the number of different probes which would need to be synthesised in order to process multiple samples (containing a plurality of target nucleic acids) in parallel.

In one embodiment, therefore, in step (a) said fragmenting a nucleic acid sample comprises separately fragmenting a plurality of nucleic acid samples, ligating to the fragments of which samples, respectively, common (or generic) nucleic acid adaptors carrying different molecular tags, and pooling said adaptor-ligated fragmented nucleic acid samples prior to step (b).

The adaptor may further comprise a recognition site for an endonuclease.

In another aspect of the method of the invention, the hybridisation and ligation steps (c) and (d) occur through resolution of a generated secondary structure using a flap endonuclease (FEN). In order to generate the secondary structure which is the substrate for the flap endonuclease, the first target-specific part of oligonucleotide A of the probe must be complementary to a portion internal to the target fragment, rather than to an end portion. Hybridisation of the probe (comprising oligonucleotide A hybridised to oligonucleotide B) to the target fragment causes the non-hybridised 5' end of the target fragment to protrude. The resulting secondary structure is recognised by a flap endonuclease which cleaves off the protruding non-hybridised 5' end of the target fragment to reveal a new 5' end which is hybridised to oligonucleotide A and is ligatable to the oligonucleotide B. Thus, the part of the single-stranded portion of the target fragment which is ligated to oligonucleotide B of the probe (i.e. the part that is hybridised to oligonucleotide A of the probe as described in step (d)) is said ligatable 5' end, and the probe-target fragment hybrid will lack a portion at the 5' end of the original, pre-probe-bound target fragment corresponding to said protruding end.

In such an embodiment, therefore, the first target-specific part of oligonucleotide A comprises at least 10 nucleotides complementary in sequence to an internal non-end portion of said single-stranded target fragment, and said annealing of said probe to said target fragment is through hybridisation of said internal non-end portion to the first target-specific part of oligonucleotide A causing the 5' end of the target fragment to form a substrate for flap endonucleolytic cleavage and further comprising cleaving said flap endonucleolytic cleavage substrate to produce a ligatable 5' end of said target fragment which is hybridised to oligonucleotide A of said probe.

As such a use of a flap endonuclease results in internal cleavage of the target fragment to generate a 5' end for ligation to oligonucleotide B of the probe, if a common nucleic acid adaptor is used said adaptor must not be ligated only to the 5' ends of the strands of the fragments. Thus, the adaptor may be ligated to both the 5' and 3' ends of the strands of the fragments (in which case the 5' end adaptor will be cleaved off during the flap cleavage step) or may be ligated to only the 3' ends of the strands of the fragments (which can be achieved by, for example, dephosphorylation of the fragments as described above).

Hence in a further embodiment, if a common (or generic) nucleic acid adaptor is non-target-specifically annealed to the ends of the fragments between steps (a) and (b), said annealed adaptor becomes ligated to the fragments only at the 3' ends, or at both the 3' and 5' ends, of the strands of the fragments, more particularly such that an adaptor is ligated to at least the 3' end of the strand of the target fragment to which, at the 5' end, oligonucleotide B of the probe is ligated in step (d).

In another aspect of the method of the invention, the probe-target fragment hybrid is circularised. In such a case enriching may involve increasing the amount of circular molecules relative to the amount of linear molecules. Thus, following the ligation step (d), an end of at least the target fragment, being the end to which the probe is not ligated (which end may in certain embodiments comprise a common nucleic acid adaptor) is rendered double-stranded in the event that said end is not double-stranded following the step (b) of rendering the fragments at least partially single-stranded (e.g. in aspects of the method wherein the fragments were made completely single-stranded). "Double-stranded" in the present context does not mean (but does encompass) that said ends are made "blunt", and "sticky" ends formed by a single-stranded overhang of 1, 2, 3, 4, 5 or 6 etc. nucleotides generated by restriction enzyme digestion are included in this meaning. Such rendering double-stranded may be achieved by any suitable method, e.g. by polymerisation from a hybridised probe 3' end or from added oligonucleotides (e.g. hexamers) annealed to the target fragment or, if present, adaptor. In embodiments in which an adaptor is ligated to the fragments, the end (comprising said adaptor) may be made double-stranded by adding an oligonucleotide complementary to the adaptor. In embodiments wherein the fragments are rendered only partially single-stranded, the ends will typically already be double-stranded and no such action is required.

Said double-stranded end of the target fragment is then non-target-specifically annealed intramolecularly with the free, non-target bound end of the probe at the other end of the probe-target fragment hybrid. As the remaining, non-target, fragments will lack ligated probe and therefore be single-stranded at the other end, such intramolecular annealing will not occur. Thus, the probe-target fragment hybrid, optionally also containing a common nucleic acid adaptor, will intramolecularly adopt a circular conformation. In this context, by "non-target-specifically" is meant that said annealing is by means which do not take advantage of or rely on (i.e. are not dependent upon) the particular nucleotide sequence of the target fragment in the sense that no knowledge of the sequence of the target fragment is required in order to effect such annealing. Hence, the means of annealing may differ according to whether or not the relevant end of the target fragment comprises an adaptor. If an adaptor is present, such annealing will include that between sticky restriction ends, as no sequence of the target fragment is required to exploit a restriction recognition sequence within the known sequence of the adaptor. However, if no adaptor is present, such annealing is limited to that between two blunt ends or two "artificial" sticky ends (such as used in TA-ligation, discussed above). In such embodiments the probe is designed to have, at the free, non-target fragment-bound end, a blunt or complementary sticky end, as appropriate, or contains a restriction endonuclease recognition sequence allowing the creation, through cleavage, of such an end. After the intramolecular-annealing of the probe-target fragment hybrid, oligonucleotide B of the probe is ligated with the corresponding strand of the double-stranded end resulting in circularisation of the hybrid.

Hence, in a further embodiment the method further comprises, between steps (d) and (e), rendering double-stranded an end of at least the target fragment, being the end to which the probe is not ligated, which end will comprise a common nucleic acid adaptor sequence in the case that such an adaptor is ligated to the fragments between steps (a) and (b); non-target-specifically annealing said double-stranded end intramolecularly with the free, non-target fragment-bound end of the probe; and ligating oligonucleotide B of the probe-target fragment hybrid with the corresponding strand of said double-stranded end to circularise said hybrid.

The selective circularisation of the target fragment in this aspect of the method can be exploited in the enriching and/or detecting step. In one embodiment, therefore, said enriching and/or detecting is by means that increases the ratio of circular to linear nucleic acids. Such enrichment or detection of circular molecules may be achieved by any suitable means, which include methods to selectively amplify circular nucleic acids, e.g., rolling circle replication (RCA), hyperbranched RCA, multiple strand displacement. Furthermore, enrichment of circular molecules may be achieved by methods to selectively remove non-circular nucleic acids, e.g. exonucleolysis. Suitable exonucleases are known, and include exonuclease I, exonuclease III, lambda exonuclease.

A number of representative preferred specific embodiments of the invention are enumerated below.

In a first such embodiment, the method of the invention comprises:

(a) fragmenting a nucleic acid sample to generate nucleic acid fragments including a target fragment containing said target nucleic acid;

(b) non-target-specifically annealing to the ends of said fragments a common nucleic acid adaptor, wherein the annealed adaptor becomes ligated to the fragments only at the 3' ends, or only at the 5' ends, of the strands of the fragments;

(c) rendering said fragments, including said target fragment, single-stranded;

(d) contacting the single-stranded fragments of step (c) with oligonucleotides A and B of a single target-specific nucleic acid probe, wherein:

(i) oligonucleotide A is a single-stranded oligonucleotide comprising at one end a first target-specific part comprising at least 10 nucleotides complementary in sequence to a portion at the end of said single-stranded target fragment other than the end to which the common nucleic acid adaptor is ligated in step (b), and comprising at the other end a second non-target-specific part which comprises a nucleotide sequence complementary to at least a portion, including one end, of oligonucleotide B of the probe, and (ii) oligonucleotide B is a single-stranded oligonucleotide which contains or carries an amplification primer binding site and optionally an element for immobilisation to a solid phase, and of which at least a portion, including one end, is complementary in sequence to the second non-target-specific part of oligonucleotide A, such that said target fragment becomes annealed to said probe through hybridisation to the first target-specific part of oligonucleotide A resulting in only one target-specific probe-binding event per target fragment;

(e) ligating oligonucleotide B of said probe to the end of said target fragment which is hybridised to oligonucleotide A of said probe to produce a probe-target fragment hybrid; and (f) enriching for said probe-target fragment hybrid through amplification by means of the amplification primer binding site in oligonucleotide B of the probe and an amplification primer binding site in the common nucleic acid adaptor, and optionally immobilising said fragment to a solid phase by means of the immobilisation element in oligonucleotide B of the probe.

Preferably, the fragmenting in step (a) is by restriction endonuclease and/or in step (c) the fragments are rendered single-stranded by denaturation.

As discussed above, the method of the invention is advantageous in that the target fragment undergoes only a single target-specific binding event with the probe, necessitating knowledge of only a single, short region of the target fragment. This is an advantage over known methods such as PCT and the Selectors of WO 2005/111236 which require knowledge of the target fragment/nucleic acid sequence at two regions (which delineate the target nucleic acid). In particular, the method of the invention facilitates the analysis of unknown nucleic acid junctions such as DNA translocation breakpoints, recombination sites and splice junctions. The single-sided ligation of the probe with the target nucleic acid fragment, containing the target nucleic acid, can be thought of as the fragments being selectively "pulled out" of the nucleic acid sample by one end (the end containing known sequence, on the basis of which the probe is designed). Providing the sample has been fragmented appropriately, i.e. to give fragments of sufficient length, the junction of interest will be located in the pulled-out fragment and may be analysed and identified by, for example, nucleic acid sequencing. The method clearly has potential application in the field of medical diagnostics, particularly given the ease with which the method may be multiplexed through the use of target-specific probes having the same enrichment elements in oligonucleotide B, and optionally the use of a common adaptor. Whilst such an adaptor, where used, will be common in terms of all "functional" elements (such as amplification elements or restriction endonuclease recognition sites), as described above distinguishable variants may be generated by adding molecular tags. Such differently-tagged adaptors may respectively be ligated to different fragmented sub-samples of the single (pooled) nucleic acid sample which is subjected to the method. In addition to allowing the rapid preparation of hundreds or thousands of samples in a single probing and enrichment step, this facilitates ease of identification of target nucleic acids enriched from such samples in parallel, which in a medical diagnostic context may be patient samples. The use of such tagged adaptors is advantageous in dramatically reducing the number of individual probes which would need to be designed and synthesised in order for the sample provenance of each targeted nucleic acid to be indicated by use of "tagged" probes. Furthermore, the probe, and if used the adaptor, may be designed to comprise the primers used for sequencing, thereby forming an amplification product that can be sequenced directly with very little additional preparation.

The single-sided ligation feature of the method further enables other useful applications. For example, the fact that a target-specific probe-binding event occurs only at one "end" of the target fragment, with the other end binding non-target-specifically to a common adaptor (where used), means that the method may have use in analysis of degraded DNA which may be present in scarce amounts, such as in histological samples (e.g. formalin-fixed, paraffin-embedded samples). Since the adaptors are non-target-specifically ligated to the target fragments, every probe-bound fragment will also have an adaptor ligated thereto even if the non-probe-bound end has been generated by degradation or e.g. physical, "random" fragmentation. As a result, the method may facilitate enrichment of nucleic acids from samples not amenable to enrichment by other methods which require target-specific binding at both ends of the target nucleic acid (e.g. PCR or methods relying on intramolecular circularisation). Further, such known methods may require the target fragment to be of a minimum length, for efficient amplification, whereas fragment length is not critical in the method of the invention. Hence, the method could be used on degraded or fragmented nucleic acid with very short average fragments, representing a suitable approach for analysis of degraded DNA in scarce amounts.

As discussed above, a further advantage of the method of the invention is the covalent nature of the connection (ligation) between the target fragment and the probe. The probe becomes directly ligated to the target fragment of the sample (not to an amplification or polymerisation product thereof), allowing the use of stringent separation conditions to effectively remove free probe and non-target fragments and other reagents leading to enrichment relative to prior art methods such as microarray capture and FISH which rely on hybridisation between the probe and the target.

The method, which in most embodiments does not rely on circularisation of the target fragment, is for that reason particularly suitable for enriching for long genomic target fragments, such as fragments over 2 kb in length which can be more difficult to circularise due to the lower proximity of fragment ends relative to shorter fragments. This makes the method very suitable for analysing, by e.g. sequencing and/or high resolution polymorphism analysis, genomic regions identified by whole genome association studies to be associated with disease states. The enrichment of long fragments is also useful in another application enabled by the method of the invention, namely haplotype analysis. If the sample is known to contain a heterozygous polymorphism, it may be possible to fragment the sample using one or more enzymes including one which recognises a site inactivated by the polymorphism. By designing probes respectively to target fragments generated by the presence and absence of cleavage at the polymorphic sites, fragments corresponding to each haplotype may separately be enriched allowing analysis/identification of the respective haplotypes. In such an aspect, the generation and enrichment of long fragments is desirable to maximise the amount of haplotype-specific nucleic acid available for analysis.

As the method generally represents a highly specific way to detect and amplify particular nucleic acids from a complex sample, it may be used in preference to known methods for analysing microbes and other exogenic pathogens in complex DNA samples. The probes of the invention are shorter and cheaper to make than padlock probes, known in the art. The foreign nucleic acid could be amplified and analysed by, e.g., sequencing, in order to characterize the infectious agent for, e.g., diagnostic or drug sensitivity screening purposes.

Unlike, e.g. PCR, the method of the invention is compatible with combinatorial oligonucleotide synthesis, e.g. on microarrays, enabling the production of large probe sets at low cost, and allows analysis single molecules.

In a second embodiment of the method of the invention, said method comprises:

(a) fragmenting a nucleic acid to generate nucleic acid fragments including a target fragment containing said target nucleic acid;

(b) rendering said fragments, including said target fragment, partially single-stranded by 3' or 5' exonuclease digestion, wherein the length of the resulting single-stranded end portion is sufficient to allow hybridisation of at least part of the single-stranded end portion of said target fragment to the probe of step (c);

(c) contacting the partially single-stranded fragments of step (b) with oligonucleotides A and B of a single target-specific nucleic acid probe, wherein:
  (i) oligonucleotide A is a single-stranded oligonucleotide comprising at one end a first target-specific part comprising at least 10 nucleotides complementary in sequence to at least part of said single-stranded portion (or more particularly to a portion at the end of said single-stranded portion) of said target fragment, and comprising at the other end a second non-target-specific part which comprises a nucleotide sequence complementary to at least a portion, including one end, of oligonucleotide B of the probe, and
  (ii) oligonucleotide B is a single-stranded oligonucleotide which contains or carries an element for immobilisation to a solid phase and optionally an amplification primer binding site, and of which at least a portion, including one end, is complementary in sequence to the second non-target-specific part of oligonucleotide A, such that said target fragment becomes annealed to said probe through hybridisation to the first target-specific part of oligonucleotide A resulting in only one target-specific probe-binding event per target fragment;

(d) ligating oligonucleotide B of said probe to the end of said target fragment which is hybridised to oligonucleotide A of said probe to produce a probe-target fragment hybrid; and (e) enriching for said probe-target fragment hybrid through immobilisation to a solid phase by means of the immobilisation element in oligonucleotide B of the probe, and optionally by amplifying said target fragment by means of the amplification primer binding site in oligonucleotide B of the probe.

Such an embodiment is particularly advantageous in that the fragments remain largely or at least partially double-stranded, i.e. are not rendered completely single-stranded. This avoids to some extent the undesirable cross-reactivity between single-stranded nucleic acid fragments and thereby reduces the incidence of hybrids which must be distinguished between. This is especially for the enrichment of long genomic sequences which are more prone to such cross-reactivity when single-stranded. Applications of the method of the invention involving the enrichment of long fragments are discussed above.

Preferably, the fragmenting in step (a) is by restriction endonuclease. In another preferred aspect there exists between steps (d) and (e) a step of contacting the probe-target fragment hybrid with a strand-displacing or a non-strand-displacing polymerase such that any gap between the target fragment-hybridised end of oligonucleotide A of the probe and the exonucleolytically-degraded end of the corresponding strand of the target fragment is filled, substantially restoring the double-strandedness of the probe-target fragment hybrid. In a further preferred aspect, the ligation step is followed by a size separation step to remove free non-target fragment-bound probes.

In a third representative specific embodiment of the method of the invention, said method comprises:

(a) fragmenting a nucleic acid sample to generate nucleic acid fragments including a target fragment containing said target nucleic acid;

(b) optionally, non-target-specifically annealing to the ends of said fragments a common nucleic acid adaptor, wherein the annealed adaptor becomes ligated to the fragments at the 3' ends or at the 3' and 5' ends of the strands of the fragments such that an adaptor is ligated to at least the 3' end of the strand of the target fragment to which, at the 5' end, oligonucleotide B of the probe is ligated in step (f);

(c) rendering said fragments, including said target fragment, single-stranded;

(d) contacting the single-stranded fragments of step (c) with oligonucleotides A and B of a single target-specific nucleic acid probe, wherein:
  (i) oligonucleotide A is a single-stranded oligonucleotide comprising at one end a first target-specific part comprising at least 10 nucleotides complementary in sequence to an internal non-end portion of said single-stranded target fragment, and comprising at the other end a second non-target-specific part which comprises a nucleotide sequence complementary to at least a portion, including one end, of oligonucleotide B of the probe, and
  (ii) oligonucleotide B is a single-stranded oligonucleotide which contains or carries at least one element for detection and/or enrichment (or more particularly detection, amplification and/or capture) of said target fragment, and of which at least a portion, including one end, is complementary in sequence to the second non-target-specific part of oligonucleotide A, such that said target fragment becomes annealed at said internal non-end portion to said probe through hybridisation to the first target-specific part of oligonucleotide A resulting in only one target-specific probe-binding event per target fragment, wherein said hybridisation causes the 5' end of the target fragment to form a substrate for flap endonucleolytic cleavage;

(e) cleaving said flap endonucleolytic cleavage substrate to produce a ligatable 5' end of said target fragment which is hybridised to oligonucleotide A of said probe;

(f) ligating oligonucleotide B of said probe to the part of the single-stranded portion of said target fragment which is hybridised to oligonucleotide A of said probe to produce a probe-target-fragment hybrid;

(g) enriching for said probe-target fragment hybrid by means of said detection and/or enrichment (or more particularly detection, capture and/or amplification) element.

In this embodiment, the use of a flap endonuclease is advantageous in that it avoids the need to identify an enzyme, e.g. a restriction endonuclease, recognition sequence near to the target nucleic acid in the nucleic acid sample. The sample may be fragmented by any one or more enzymes, even if such enzymes are not known to cut in the proximity of the target nucleic acid. Alternatively, non-sequence-specific fragmentation methods, which produce fragment ends of unpredictable sequence, such as physical methods, e.g. sonication or nebulisation, may be used. In such an embodiment the probe is designed to target a region of known sequence of the target nucleic acid which is internal to a fragment, i.e. is not situated at a fragment end as in other embodiments. Because of this, the sequence at the fragment ends is not important and does not need to be known. The flap endonuclease, recognising the secondary structure (protruding (non-hybridised) 5' region of the target fragment hybridised to the probe), cleaves the fragment to create a "new" 5' end which is hybridised to oligonucleotide A of the probe and is ligatable to oligonucleotide B. The method of the invention is therefore not limited the use of sequence-specific fragmentation of the sample, or to instances wherein the region of known sequence of the target nucleic acid contains an endonuclease recognition sequence.

Preferably, said fragmenting in step (a) is by restriction endonucleolysis and/or in step (c) said fragments are rendered single-stranded by denaturation. Also preferred is that oligonucleotide B contains or carries an amplification primer binding site and optionally an element for immobilisation to a solid phase such that in step (g) said enriching is through amplification by means of the amplification primer binding site in oligonucleotide B of the probe or, if a common nucleic acid adaptor is non-target-specifically annealed to the ends of the fragments between in step (b), said amplification is by means of the amplification primer binding site in oligonucleotide B of the probe and an amplification primer binding site in the common nucleic acid adaptor. In a further preferred aspect, between steps (f) and (g) there exists a step of size-selecting the probe-target fragment hybrid by, e.g., gel purification.

In a fourth representative specific embodiment, the method of the invention comprises:

(a) fragmenting a nucleic acid sample to generate nucleic acid fragments including a target fragment containing said target nucleic acid;

(b) optionally, non-target-specifically annealing to the ends of said fragments a common nucleic acid adaptor, wherein the annealed adaptor becomes ligated to the fragments only at the 3' ends, or only at the 5' ends, of the strands of the fragments;

(c) rendering said fragments, including said target fragment, at least partially single-stranded, wherein the single-stranded portion includes an end portion and wherein the length of said single-stranded portion is sufficient to allow hybridisation of at least part of the single-stranded portion of said target fragment to the probe of step (d);

(d) contacting the at least partially single-stranded fragments of step (c) with oligonucleotides A and B of a single target-specific nucleic acid probe, wherein:

(i) oligonucleotide A is a single-stranded oligonucleotide comprising at one end a first target-specific part comprising at least 10 nucleotides complementary in sequence to at least part (or more particularly to a portion at the end) of said single-stranded portion of said target fragment, wherein if a common nucleic acid adaptor is ligated to the fragments according to optional step (b) said first target-specific part comprises at least 10 nucleotides complementary in sequence to a portion at the end of said at least partially single-stranded target fragment other than the end to which the common nucleic acid adaptor is ligated; and comprising at the other end a second non-target-specific part which comprises a nucleotide sequence complementary to at least a portion, including one end, of oligonucleotide B of the probe, and (ii) oligonucleotide B is a single-stranded oligonucleotide which contains or carries at least one element for detection and/or enrichment (or more particularly detection, amplification and/or capture) of said target fragment, and of which at least a portion, including one end, is complementary in sequence to the second non-target-specific part of oligonucleotide A, such that said target fragment becomes annealed to said probe through hybridisation to the first target-specific part of oligonucleotide A resulting in only one target-specific probe-binding event per target fragment;

(e) ligating oligonucleotide B of said probe to the part of the single-stranded portion of said target fragment which is hybridised to oligonucleotide A of said probe to produce a probe-target-fragment hybrid;

(f) if necessary rendering double-stranded an end of at least the target fragment, being the end to which the probe is not ligated, which end will comprise a common nucleic acid adaptor sequence in the case that such an adaptor is ligated to the fragments according to optional step (b);

(g) non-target-specifically annealing the double-stranded end of step (f) intramolecularly with the free, non-target fragment-bound end of the probe;

(h) ligating oligonucleotide B of the probe-target fragment hybrid with the corresponding strand of the double-stranded end of step (f) to circularise said hybrid; and (i) enriching for said probe-target fragment hybrid by means that increases the ratio of circular to linear molecules.

By circularising the probe-target fragment hybrid, in this embodiment enrichment or detection may advantageously be based on the circularised nature of said hybrids in contrast to the linear form of the non-target fragments.

The step (f) of rendering double-stranded an end of at least the target fragment will not be necessary in embodiments wherein the fragments are rendered only partially single-stranded in part (c) as in such cases the fragment end other than that to which the probe becomes ligated will remain double-stranded. In instances where such rendering double-stranded is necessary, this is preferably achieved by polymerisation from the target fragment-hybridised end of oligonucleotide A of the probe (in cases where this end is a 3' end) or, when a common nucleic acid adaptor is ligated to the fragments, by annealing of an oligonucleotide complementary thereto. The non-target-specific annealing of step (g) may be by blunt or artificially-created sticky end annealing, i.e. by annealing means which does not rely on knowledge of sequence of the target fragment. If a common nucleic acid adaptor is ligated to the target fragment, the annealing may be between sticky ends generated through sequence-specific digestion of the adaptor and a corresponding sticky end at the free end of the probe.

The enrichment step may involve selective removal of non-circular nucleic acids by e.g. exonuclease treatment. Preferably a mixture of exonucleases enabling degradation of linear double-stranded DNA, for example including exonuclease III, lambda exonuclease and exonuclease I, is used, though any of these or any other suitable exonucleases may be used alone. Alternatively, the circular:linear nucleic acid molecule ratio is increased by selectively amplifying the circularised probe-target fragment hybrid, such as by RCA, hyperbranched RCA or multiple strand displacement.

The invention provides kits for use in the above-described methods. Such a kit will comprise at least an oligonucleotide B and one or more oligonucleotides A, and one or more restriction endonucleases and/or a common nucleic acid adaptor or a set of such adaptors which differ from each other only by molecular tags and/or annealing ends. The oligonucleotide B of the kit may comprise at least one detection and/or enrichment element (more particularly at least one of a detection, capture and/or amplification element) as defined above, and optionally also a cleavage site such as a recognition sequence for an endonuclease. Where one or more restriction endonucleases are included in the kit, such endonucleases will be those which fragment a particular target in a way which renders useful the one or more oligonucleotides A of the kit. If the kit comprises one or more common nucleic acid adaptors, such adaptors will have an annealing end compatible with the sticky ends generated by the one or more restriction endonucleases which fragment a particular target in a way which renders useful the one or more oligonucleotides A of the kit, regardless of whether such one or more restriction endonucleases are included in the kit. The one or more adaptors may contain an amplification and/or sequencing primer binding site, and/or a cleavage site.

The kit may further comprise one or any combination of two or more of the following components. Thus, the kit may contain a ligase for ligating the end of oligonucleotide B of the probe to the target nucleic acid fragment, particularly a ligase as specifically mentioned above in connection with the step of ligating the target fragment to the probe. A solid phase as defined above, to which the oligonucleotide B of the kit is immobilisable, or immobilised, may be included. Alternatively or additionally, an amplification or sequencing primer specific for a primer binding site in oligonucleotide B (i.e. corresponding to sequences of the oligonucleotide B) may be included, and optionally also a polymerase and/or other reagents required for amplification and/or sequencing such as nucleotides, buffers, ions, etc. Means for cleaving the probe at the cleavage site in oligonucleotide B, such as a restriction endonuclease, may be included. For embodiments of the method of the invention employing an exonuclease for rendering the sample fragments single-stranded, the kit may include such an enzyme, particularly such an enzyme as specifically mentioned above in connection with the rendering single-stranded step. A polymerase may be included for filling any gap between oligonucleotide A and the partially-degraded strand of the probe-hybridised target fragment and/or for extending a 3' end of oligonucleotide A in order to render the non-probe end of the probe-target fragment hybrid double-stranded in certain embodiments. Optional other kit components include a dephosphorylase (phosphatase) such as discussed above, a kinase for adding 5' phosphates for selective ligation, a polymerase (such as T4 DNA polymerase) for blunting overhanging (sticky) restriction fragment ends, free adenosine, a polymerase for adding same to blunted fragment ends, random hexamers for priming polymerisation in order to render the non-probe end of the probe-target fragment hybrid double-stranded in certain embodiments or for multiple strand displacement amplification, qPCR reagents e.g. fluorescently-labelled nucleotides or Taqman® probes, a primer or primers for RCA or hyperbranched RCA, and a flap endonuclease for fragmenting the nucleic acid sample.

The kit may optionally also contain appropriate primers, amplification/sequencing reagents and/or cleaving means as mentioned above for use in connection with an amplification and/or sequencing primer binding site, and/or a cleavage site, in a common nucleic acid adaptor which may be employed in the methods of the invention. Also optionally included in such a kit are single-stranded oligonucleotides corresponding to either strand of the double-stranded adaptor, in order to render the non-probe end of the probe-target fragment hybrid double-stranded in certain embodiments. In certain embodiments hybridisation/ligation of the target fragment to the probe is mediated by a flap endonuclease and accordingly the kit may further include such an enzyme and optionally appropriate co-factors.

The kit components may be present in separate containers, or one or more of the components may be present in the same container, where the containers may be storage containers and/or containers that are employed during the assay for which the kit is designed.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a remote site. Any convenient means may be present in the kits.

Accordingly, in a further embodiment of the invention is provided a kit for detecting or enriching for a target nucleic acid present in a nucleic acid sample, said kit comprising:

(a) an oligonucleotide B, being a single-stranded oligonucleotide which may contain or carry at least one element for detection and/or enrichment (or more particularly detection, amplification and/or capture) of a target fragment, and of which at least a portion, including one end, is complementary in sequence to the second non-target-specific part of an oligonucleotide A, wherein said target fragment and said second non-target-specific part are as defined above, and;

(b) one or more oligonucleotides A, being a single-stranded oligonucleotide comprising at one end a first target-specific part comprising at least 10 nucleotides complementary in sequence to at least part of the single-stranded portion of a target fragment, and comprising at the other end a second non-target-specific part which comprises a nucleotide sequence complementary to at least a portion, including one end, of oligonucleotide B, wherein said single-stranded portion and said target fragment are as defined above, and;

(c)

(i) one or more restriction endonucleases, and/or;

(ii) a common nucleic acid adaptor, or a plurality of variants of such an adaptor which differ from each other at a carried molecular tag and/or at the end by which the adaptor anneals to said fragments.

The invention will be further described with reference to the following non-limiting Examples with reference to the following drawings in which:

FIG. 1 shows a particular embodiment of the method.

The nucleic acid sample is restriction enzyme digested;

A common double-stranded adaptor is designed to ligate selectively to either the 3' or 5' ends of the fragments. This is achieved by selective phosphorylation/dephosphorylation of the adaptor or the fragments (phosphorylated ends shown as "P");

The fragments are denatured;

The probe is annealed to the target fragment;

The probe is ligated to the target fragment;

Optionally the probe is equipped with a function for immobilization to a solid phase;

The target fragment is amplified using common sequences in the adaptor and oligonucleotide B of the probe.

Figure 2:
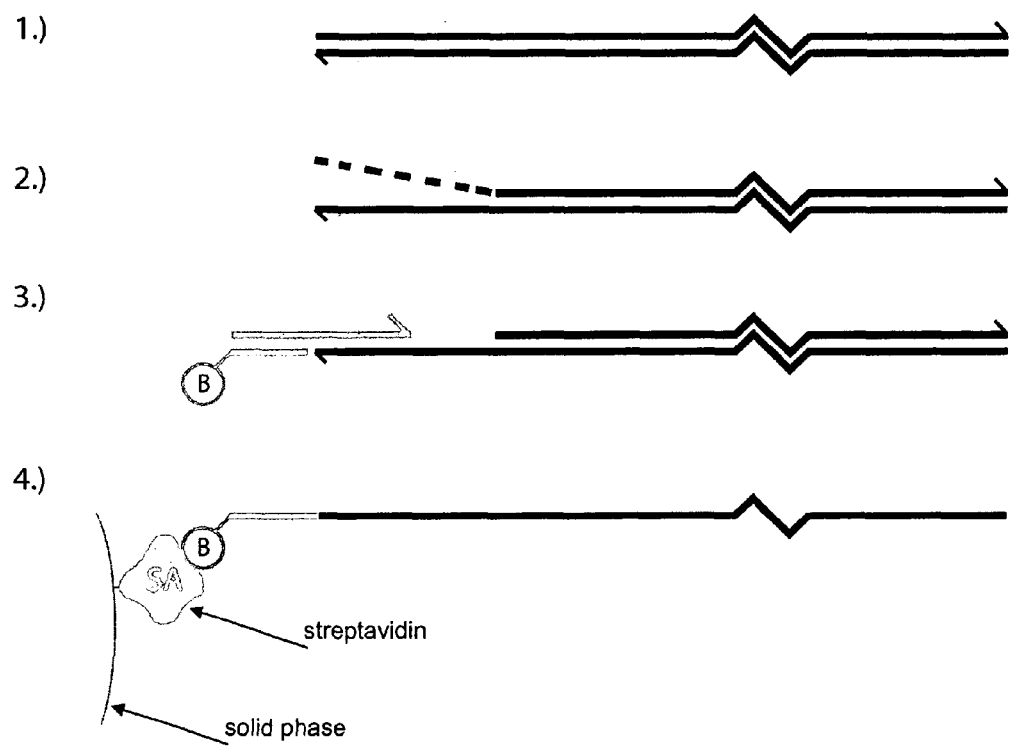

FIG. 2 shows a further particular embodiment of the method.

The nucleic acid sample is restriction enzyme digested;

A portion of either the 5'- or 3'-ends of all fragments are made single-stranded by exonucleolysis, whilst a middle portion remains double-stranded;

The probe is designed to hybridize with one of the two single stranded ends of the target fragment so that a junction susceptible to ligation is created;

The probe is ligated to the target fragment;

The probe is equipped with a function such as a biotin molecule (shown as "B") for solid phase enrichment;

Optionally the target fragment is amplified using a common sequence in oligonucleotide B of the probe.

Figure 3:
Figure 3:
Figure 3:
Figure 3:

FIG. 3 shows a further particular embodiment of the method.

The sample nucleic acid is fragmented using physical or enzymatic means;

Optionally, a common double-stranded adaptor is ligated specifically to the 3' ends of the fragments by e.g. dephosphorylating the sample and using a phosphorylated adaptor (phosphorylated ends shown as "P");

The fragments are denatured;

The probe is annealed to the target fragment to form a substrate for a flap endonucleolytic cleavage of the target fragment 5' end;

The probe is ligated to the target fragment;

Optionally the probe is equipped with a function for solid phase immobilization and enrichment;

The probe is amplified and or detected using the common sequences in oligonucleotide B of the probe and/or optionally the adaptor.

Figure 4:
Figure 4:
Figure 4:
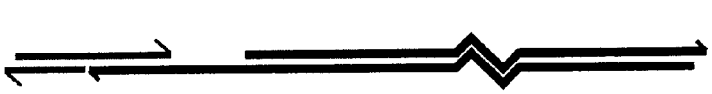
Figure 4:
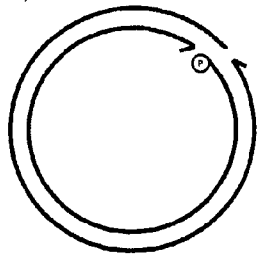
Figure 4:
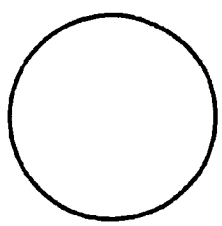

FIG. 4 shows a further particular embodiment of the method.

The target fragment is equipped with a probe according to any of the embodiments of the method of the invention;

The distal part of the target fragment with respect to the probe is made double-stranded where this is not already the case. This may, for example, be mediated by polymerisation initiated from a hybridised probe 3' end or by annealing of hexamers followed by polymerisation;

The probe is designed to allow intramolecular circularisation with the distal end of the probe-target fragment hybrid molecule, formed by ligation;

The intramolecular ligation may, e.g., be by sticky end ligation or blunt end ligation;

Circularised probe-target fragment hybrids are then enriched for using rolling circle amplification (RCA), hyperbranched RCA, multiple strand displacement, exonucleolysis or other methods that increase the ratio between circular and linear molecules.

Figure 5:
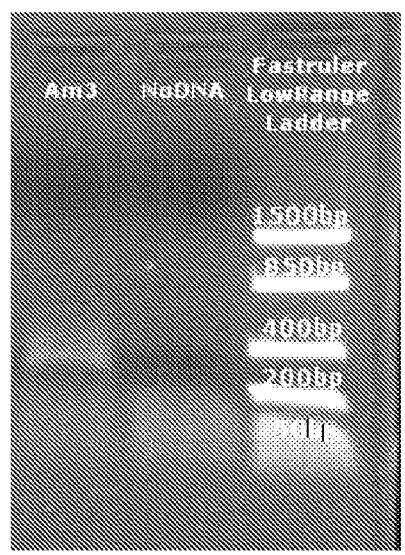

FIG. 5 shows the amplification products from the amplification reaction. Am3=amine adaptor ligated to fragments. NoDNA=negative control where no genomic DNA was included in the hybridization reaction. All 17 fragments that were selected are between 200 and 450 nucleotides long.

Figure 6:
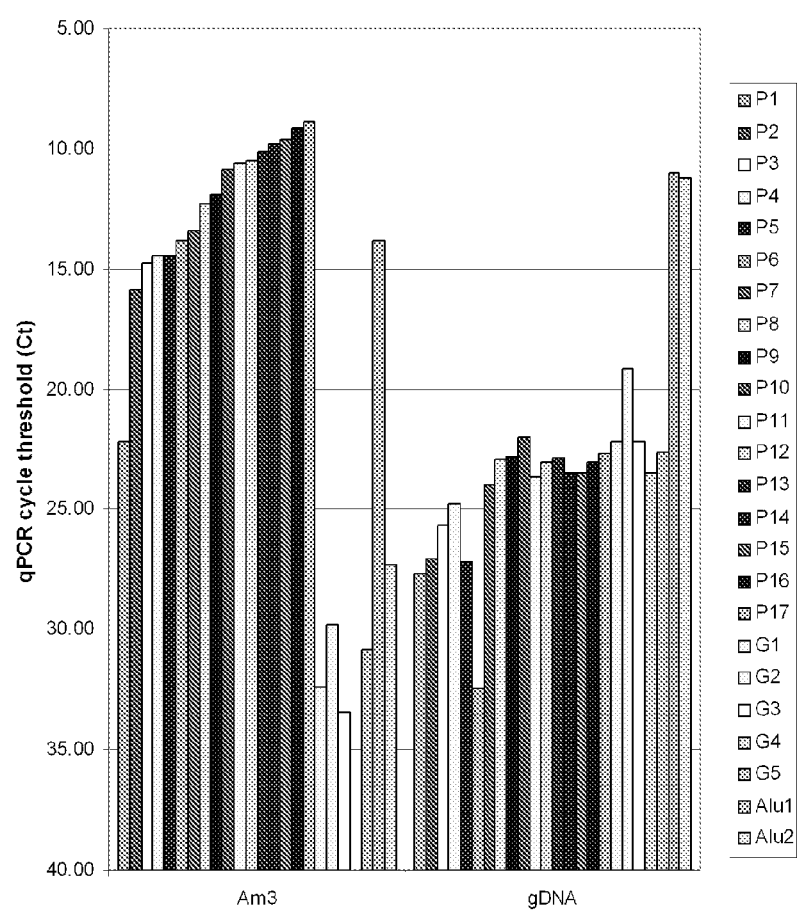

FIG. 6 shows qPCR readout of amine blocked selection. Ct values for each primer pair are shown left to right along the x-axis, corresponding to descending order of the primer pairs listed in the key.

EXAMPLES

Example 1

Restriction enzyme digested human genomic DNA was incubated with T4 DNA polymerase in order to generate blunt ends. Subsequently a 3' adenosine overhang was generated by addition of Taq polymerase and the product was ligated to an adaptor with 3' protruding thymidines in separate reactions using T4 DNA ligase. Seventeen in silico designed probe-oligonucleotide As together with a common probe-oligonucleotide B were then added to the reaction mix. The reaction was then heat denatured and the probes were allowed to hybridize to the single stranded ends of 17 specific genomic fragments in the restriction enzyme digested genomic DNA sample. After hybridization the probes were captured by a solid phase (beads) using a biotin on the probe. Following stringent washing probes were ligated on the beads and all fragments were amplified by PCR using one common primer pair located in the probe and adaptor respectively. The results were analyzed by gel electrophoresis and qPCR.

The sequences of the 17 probe-oligonucleotide As, adaptor, probe-oligonucleotide B and primer pair are outlined in Table 1. The "amine" terminology used in connection with the adaptors indicates that one end of the adaptors (the end not intended to ligate with the nucleic acid fragments) is "protected" from such ligation by an amine ($NH_2$) group.

TABLE 1

| Target ID | Probe-oligonucleotide A |
|---|---|
| ROI_1 (SEQ ID NO: 1) | ACAACGGGAATTCAAATCAAGATGGTGGCCACACCCCATGCGTACCAATGGATGCGGTCT |
| ROI_2 (SEQ ID NO: 2) | AAAAGAAGCAGGGAGTCAACTTCCTGCACCTTTTAACTCTACGTACCAATGGATGCGGTCT |
| ROI_3 (SEQ ID NO: 3) | CACCTGATGATGGTCMTGGAGGCATTGTTCTGATTCTTTGCGTACCAATGGATGCGGTCT |
| ROI_4 (SEQ ID NO: 4) | CACACACCAGACTTGTCAGCCTCCCAAAGAGCCATGCTCCCGTACCAATGGATGCGGTCT |
| ROI_5 (SEQ ID NO: 5) | CACTGGCTGAGGTGCCAGATGGGTCTCCTGGCTATAGGGACGTACCAATGGATGCGGTCT |
| ROI_6 (SEQ ID NO: 6) | TCTTCAAAGGCAAGGTTTCAATTATGCAAAAACCACCTTACGTACCAATGGATGCGGTCT |
| ROI_7 (SEQ ID NO: 7) | AAYCTACGGCCATGGCAGGTAAGACGCTGCAGGGAAGCAGCGTACCAATGGATGCGGTCT |
| ROI_8 (SEQ ID NO: 8) | TGCTGTTTCCACATAGCAGAGGCTGTTAGGCTCAGAGCTACGTACCAATGGATGCGGTCT |
| ROI_9 (SEQ ID NO: 9) | GGGGTGCTTGAGAGCTTCGCTTGCACTTATTCGCCAACTACGTACCAATGGATGCGGTCT |
| ROI_10 (SEQ ID NO: 10) | TCTGTGGTAGTACCTAGAATAAGCTATGCAGCCTCTCTGACGTACCAATGGATGCGGTCT |
| ROI_11 (SEQ ID NO: 11) | GACAGCCGTGTATTACCCAATATCCCCAAAGGCAGCCTTACGTACCAATGGATGCGGTCT |
| ROI_12 (SEQ ID NO: 12) | GGTTCTGCTCCTCATCCGCTGTGGATCAGATGTGCTCTGACGTACCAATGGATGCGGTCT |
| ROI_13 (SEQ ID NO: 13) | AATCTTTTGGAACCCAATTGGTCATATTTCCTTCTACTTACGTACCAATGGATGCGGTCT |
| ROI_14 (SEQ ID NO: 14) | TGCTGGTTCTCAAATCCGAACGCTCTGTGATAAATTTCTGCGTACCAATGGATGCGGTCT |
| ROI_15 (SEQ ID NO: 15) | CTCACAGAAACCAAAGCGTTTCCCAACAGCACGTTTCCTGCGTACCAATGGATGCGGTCT |
| ROI_16 (SEQ ID NO: 16) | AATTTTAGAAATCCTTRAATTTTCCATGTCTACATTCATGCGTACCAATGGATGCGGTCT |
| ROI_17 (SEQ ID NO: 17) | GTTCTATGAAAAGAAAAAAAGAAACGATTAAGGTTTCATGCGTACCAATGGATGCGGTCT |

| Adaptor 5'-3' | |
|---|---|
| Amine plus (SEQ ID NO: 18) | CGTTATCAACCTGGGTCCGA |
| Amine minus (SEQ ID NO: 19) | TCGGACCCAGGTTGATAACGT |

TABLE 1-continued

| Target ID | Probe-oligonucleotide A |
|---|---|
| | Probe-oligonucleotide B 5'-3' |
| (SEQ ID NO: 20) | CTGGACCTTAATCGTGTGCGAGACCGCATCCATTGGTACG |
| | Common primer pair 5'-3' |
| Fwd primer (SEQ ID NO: 21) | AGACCGCATCCATTGGTACG |
| Rev primer (SEQ ID NO: 22) | TCGGACCCAGGTTGATAACG |

Restriction Enzyme Digestion

Genomic DNA was restriction enzyme digested using restriction 10 different restriction enzymes combined in 5 separate reactions outlined in Table 2. 10 units of each restriction enzyme were used to digest 1 μg of DNA at 37° C. for 2 h.

TABLE 2

| Target ID | Target length (bp) | Restriction reaction | 5' end | 3' end | qPCR primer pair |
|---|---|---|---|---|---|
| ROI_1 | 314 | XmnI/HpyCH4V | blunt | blunt | P01 |
| ROI_2 | 305 | BfaI/AlwI | 5'o-h | 5'o-h | P02 |
| ROI_3 | 395 | XmnI/HpyCH4V | blunt | blunt | P03 |
| ROI_4 | 260 | HpyAV/DraI | blunt | blunt | P04 |
| ROI_5 | 386 | NspI/MlyI | 3'o-h | 3'o-h | P05 |
| ROI_6 | 288 | DdeI/BspHI | 5'o-h | 5'o-h | P06 |
| ROI_7 | 270 | HpyAV/DraI | blunt | blunt | P07 |
| ROI_8 | 264 | BfaI/AlwI | 5'o-h | 5'o-h | P08 |
| ROI_9 | 287 | BfaI/AlwI | 5'o-h | 5'o-h | P09 |
| ROI_10 | 205 | DdeI/BspHI | 5'o-h | 5'o-h | P10 |
| ROI_11 | 301 | DdeI/BspHI | 5'o-h | 5'o-h | P11 |
| ROI_12 | 226 | DdeI/BspHI | 5'o-h | 5'o-h | P12 |
| ROI_13 | 361 | DdeI/BspHI | 5'o-h | 5'o-h | P13 |
| ROI_14 | 355 | XmnI/HpyCH4V | blunt | blunt | P14 |
| ROI_15 | 226 | XmnI/HpyCH4V | blunt | blunt | P15 |
| ROI_16 | 385 | DdeI/BspHI | 5'o-h | 5'o-h | P16 |
| ROI_17 | 365 | DdeI/BspHI | 5'o-h | 5'o-h | P17 |

TABLE 3

Primer pairs used

| Primer pair | Target | Forward | Reverse |
|---|---|---|---|
| P1 | ROI_1 | TTCCCCACTGACAGCCTC (SEQ ID NO: 23) | GACCCAAAACCCAAAATGG (SEQ ID NO: 24) |
| P2 | ROI_2 | CCCCTGTGGACCTCAACC (SEQ ID NO: 25) | TGCTTGAAAAGCCAGTGC (SEQ ID NO: 26) |
| P3 | ROI_3 | TCACGGAGGCATTCTAAAGTC (SEQ ID NO: 27) | TTGATGCCCCCAAGAATC (SEQ ID NO: 28) |
| P4 | ROI_4 | CCAAGGGCATCCAGTTTG (SEQ ID NO: 29) | GGGGCCACACACATCTTC (SEQ ID NO: 30) |
| P5 | ROI_5 | ACCTTCCTTGCCCCTCTG (SEQ ID NO: 31) | TCCAGCCGTCAACTCCTC (SEQ ID NO: 32) |
| P6 | ROI_6 | TGAGCAAATCCAGTCAGGG (SEQ ID NO: 33) | ACTGTGTGGCAAACTGCG (SEQ ID NO: 34) |
| P7 | ROI_7 | TGAAAAGAGAACATGGGGG (SEQ ID NO: 35) | GAGAAGCCCTTTCCAGGC (SEQ ID NO: 36) |
| P8 | ROI_8 | CTCACCTTTGCGCCTCTG (SEQ ID NO: 37) | GAGGTGGAGAAACGCAGG (SEQ ID NO: 38) |
| P9 | ROI_9 | GCGAAGCTCTCAAGCACC (SEQ ID NO: 39) | CATTGAGTCTGGAGTGGAGC (SEQ ID NO: 40) |
| P10 | ROI_10 | CTCCTCTGTGCAGGTGGG (SEQ ID NO: 41) | GGATGTCCTCAAGCCGTG (SEQ ID NO: 42) |
| P11 | ROI_11 | GGAAACTCCCCTTACCCG (SEQ ID NO: 43) | TGTTGCCCATGTCAGCAC (SEQ ID NO: 44) |
| P12 | ROI_12 | GTCCCATGGTGCTTGCAG (SEQ ID NO: 45) | ATCTCTGGCTCCGTCGTG (SEQ ID NO: 46) |
| P13 | ROI_13 | TTTGACGGGCATCCTTTC (SEQ ID NO: 47) | ACAGGCGAAGGAGGTGTG (SEQ ID NO: 48) |
| P14 | ROI_14 | GTGACCTGCCACCTCCAG (SEQ ID NO: 49) | GCTGGCGTAAAGGTGAGG (SEQ ID NO: 50) |
| P15 | ROI_15 | AATGGCAACGACGGGTAG (SEQ ID NO: 51) | CAAACGCTCTGAGACAGCC (SEQ ID NO: 52) |
| P16 | ROI_16 | GCCTGGCAGAGCTGAATC (SEQ ID NO: 53) | CCAAGCACCTAACAGGCATC (SEQ ID NO: 54) |
| P17 | ROI_17 | CCGAAACATGGATTTGGC (SEQ ID NO: 55) | TCAACCGGCAAAGTCAGC (SEQ ID NO: 56) |
| G1 | Not enriched | GACAGCTCCCCACACACC (SEQ ID NO: 57) | TTCCTGCCTGAGCTGACC (SEQ ID NO: 58) |

TABLE 3-continued

Primer pairs used

| Primer pair | Target | Forward | Reverse |
|---|---|---|---|
| G2 | Not enriched | TGCCTCTCTTGCTCTGGG (SEQ ID NO: 59) | GTGGGCATGGGTCAGAAG (SEQ ID NO: 60) |
| G3 | Not enriched | ACAGCTGCCCACTTCTGG (SEQ ID NO: 61) | GCGAGGACCAAACTCAGG (SEQ ID NO: 62) |
| G4 | Not enriched | ATTCAGGCGCTTTGCATC (SEQ ID NO: 63) | AGGCTGGTCACATGGGTG (SEQ ID NO: 64) |
| G5 | Not enriched | CATGGTCTTGGACTGGGC (SEQ ID NO: 65) | AGCTCGATCTTCATGCGG (SEQ ID NO: 66) |
| Alu1 | Alu repeat | GCGCGGTGGCTCACGCCTGT (SEQ ID NO: 67) | CCTCCCAAAGTGCTGGGATT (SEQ ID NO: 68) |
| Alu2 | Alu repeat | CGCCACTGCACTCCAGCCTG (SEQ ID NO: 69) | CGATCTCCTGACCTCATGAT (SEQ ID NO: 70) |

Blunt Ending Fragments Using T4 DNA Polymerase

Blunt ends were generated from 0.5 µg of digested genomic DNA using 3 Units of T4 polymerase and 0.1 mM dNTP in 1× Special Buffer (50 mM KAc, 3 mM MgAc, 20 mM TrisAc, 1 mM DTT, 0.1 µg/µl BSA) in a total reaction volume of 15 µl. Two separate enrichment reactions were performed and one additional negative control reaction without addition of restriction enzyme digested genomic DNA. All reactions were incubated at 12° C. for 15 min and 65° C. for 20 min.

Shrimp Alkaline Phosphatase (SAP)

5' phosphates were removed by addition of 1 U of SAP in 5 µl 1× Special Buffer. Reactions were incubated at 37° C. for 15 min and 65° C. for 15 min.

Addition of dATP 3' Overhangs

Protruding adenosine 3' ends were generated by addition of 5 U Taq polymerase, 0.5 mM dATP in 5 µl 1× Special Buffer. Reactions were incubated at 72° C. for 20 min.

TA-Ligation to Adaptors

Fifteen Units of T4 DNA Ligase was used to ligate 0.83 µM amine modified adaptor (5× the concentration of all fragment ends) and 1 mM ATP to the genomic DNA. Total reaction volumes were 30 µl in 1× Special Buffer. Reactions were incubated over night at 16° C. and heat inactivated at 65° C. for 20 min.

Enrichment

Probe hybridizations were performed using 12.5 µl of the 30 µl reactions, 0.1 nM of each probe-oligonucleotide A and 7.73 nM of the biotinylated probe-oligonucleotide B, 27.27% formamide and 0.7× Bind&Wash buffer in a total reaction volume of 27.5 µl (1×B&W: 1 M NaCl, 5 mM EDTA, 0.1% Tween-20, 10 mM Tris-HCl pH 7.5). Reactions were incubated at:

95° C. for 10 min, 75° C. for 30 min, 68° C. for 30 min, 62° C. for 30 min, 55° C. for 30 min, 46° C. for 10 h, 10° C. overnight.

Probes were captured using 10 µg streptavidin-coated magnetic beads (Dynabeads M-280, Invitrogen) in a total volume of 200 µl 1.09×B&W buffer and 3.8% Formamide. Reactions were incubated at room temperature for 1 h with rotation.

The supernatant was removed using a magnet rack and reactions were washed with 200 µl 1×B&W buffer and 20% formamide at 46° C. for 30 min with rotation.

The washing solution was removed using a magnet rack and beads washed with 200 µl 1×B&W buffer at 46° C. for 10 min with rotation.

After removing the washing buffer using a magnet rack reactions were phosphorylated and ligated in the same reaction by addition of 5 U PNK, 1 mM ATP, 12.5 U Ampligase, 1× Ampligase buffer, 1 mM NAD and 0.2 µg/µl BSA in a total volume of 50 µl. Reactions were incubated at 37° C. for 30 min and 55° C. for 1 h.

The ligation reactions were removed using a magnetic rack. PCR was performed using 1.5 U Taq Platinum polymerase, 0.1 µM primers, 0.2 mM of each dATP, dUTP, dCTP and dGTP, 2 mM MgCl$_2$ and 1×PCR buffer in a final volume of 50 µl.

PCR reactions were incubated at 95° C. for 3 min followed by 40 cycles at 95° C. for 30 sec, 55° C. for 1 min and 72° C. for 1 min and a final step at 72° C. for 10 min.

Reactions were heated to 95° C. for 5 min and supernatants were transferred to new tubes using a magnet rack.

Five microlitres of the amplified products were analyzed using 1% ethidium bromide-containing agarose gel electrophoresis and the results are presented in FIG. 5.

qPCR was then performed on the enriched fragments. The qPCR analysis used 17 primer pairs, one targeting each of the 17 enriched genomic fragments (P1-17, Table 3) as well as 5 primer pairs amplifying regions that were not enriched (G1-5). Two PCR reactions using primers targeting Alu-repeats were also performed (Alu1-2). 10 µl 1:100 diluted PCR product was used in each reaction with 0.9 Units Taq Platinum polymerase, 0.17 µM primer, 0.2 mM dNTP, 1×SYBR® Green I, 10% DMSO and 2 mM MgCl2 in 1×PCR buffer to a total volume of 30 µl.

Example 2

Genomic DNA from DNA samples of interest is digested with a rare-cutting restriction enzyme. It may be preferable to use a type IIs enzyme, because thereby restriction fragments will not share end sequences. The enzyme should furthermore leave 5' overhangs in order to be suitable for processing in the subsequent step.

Treat the digested DNA with exonuclease III for a predetermined time, adjusted to remove a suitable length of the 3' end sequence of all restriction fragments.

Add a large amount of probe-oligonucleotide As whose 5' "halves" are complementary to (one of) the 5' ends of the restriction fragments that should be isolated, while the other "halves" of the oligonucleotide As contain a standard sequence. The aim is to reach all copies of the restriction fragments. Preferably each half of the oligonucleotide As encompasses 30 or so nucleotides.

Also add an even greater amount of probe-oligonucleotide Bs complementary to the standard sequence of the oligonucleotide As under step 3, and modified at the 5' ends for efficient capture on a solid phase either before or after being ligated to the genomic restriction fragments.

The digested genomic DNA (step 2) and probe oligonucleotides (steps 3 and 4) are incubated under suitably stringent conditions.

Add DNA ligase and cofactors so that probes now become covalently joined to the appropriate genomic DNA fragments.

If desired, add a strand-displacing polymerase and nucleotides to repair the ExoIII-digested ends of the restriction fragments, also copying the covalently joined oligonucleotides.

If ligation was performed in solution, then free probes can now optionally be removed by a simple size separation step.

If ligation was performed in solution, the probes that were joined to the restriction fragments by ligation are next immobilized on a solid-phase. An attractive mechanism for capture on solid support is through click chemistry, but many alternatives can be contemplated, including via biotin-streptavidin. The nature of the solid phase is also important. Possibly very small particles could be used to efficiently reach all oligonucleotides, and then prevent movement of the modified DNA through a gel. Alternatively, a chromatographic matrix could be extensively modified with groups that can be reacted covalently or non-covalently with ones on oligonucleotide B (step 4).

Separate the particles/matrix from DNA remaining in solution.

Release the captured fragments by digestion with an enzyme designed to cleave the immobilized oligonucleotides, e.g. using a rarely-cutting restriction site included in oligonucleotide B on the solid phase (step 4).

If required the released and fragmented DNA can now be ligated again to give rise to double-stranded DNA circles or linear concatemers that can be amplified by whole-genome amplification procedures. Alternatively the released DNA can be directly applied for sequencing.

The invention claimed is:

1. A method for detecting or enriching for a target deoxyribonucleic acid (DNA) present in a nucleic acid sample, said method comprising:
   (a) fragmenting a nucleic acid sample to generate nucleic acid fragments including a target fragment containing said target DNA;
   (b) non-specifically ligating an adaptor sequence to an end of said fragments, wherein the adaptor sequence becomes ligated to an end of a strand of said fragments and wherein the end of said fragments to which said adaptor sequence is ligated is the other end of the same strand to which oligonucleotide B of the probe is ligated in step (e);
   (c) rendering said fragments, including said target fragment, at least partially single-stranded, wherein the single-stranded portion includes an end portion and wherein the length of said single-stranded portion is sufficient to allow hybridisation of at least part of the single-stranded portion of said target fragment to the probe of step (d), wherein said rendering is done by denaturation or using an exonuclease;
   (d) contacting the at least partially single-stranded fragments of step (c) with oligonucleotides A and B of a single target-specific nucleic acid probe, wherein:
      (i) oligonucleotide A is a single-stranded oligonucleotide comprising at one end a first target-specific part comprising at least 10 nucleotides complementary in sequence to at least part of said single-stranded portion of said target fragment, and comprising at the other end a second non-target-specific part which comprises a nucleotide sequence complementary to at least a portion, including one end, of oligonucleotide B of the probe, and
      (ii) oligonucleotide B is a single-stranded oligonucleotide which may contain or carry at least one element for detection and/or enrichment of said target fragment, and of which at least a portion, including one end, is complementary in sequence to the second non-target-specific part of oligonucleotide A,
   such that said target fragment becomes annealed to said probe through hybridisation to the first target-specific part of oligonucleotide A resulting in only one target-specific probe-binding event per target fragment;
   (e) directly or indirectly ligating oligonucleotide B of said probe to the part of the single-stranded portion of said target fragment which is hybridised to oligonucleotide A of said probe to produce a probe-target fragment hybrid; and
   (f) detecting or enriching for said probe-target fragment hybrid.

2. The method of claim 1 for detecting or enriching for a plurality of target DNAs, wherein in step (d) said target fragments are contacted with oligonucleotides A and B of a plurality of nucleic acid probes, each having an oligonucleotide A with a different first target-specific part, whereby a plurality of different target fragments may be respectively annealed to said probes.

3. The method of claim 2, wherein in said plurality of nucleic acid probes oligonucleotide B comprises a common sequence which is the same in each probe.

4. The method of claim 3, wherein said common sequence in each probe comprises the detection and/or enrichment element.

5. The method of claim 1, wherein the length of the first target-specific part of oligonucleotide A in step (d) is at least 20 nucleotides.

6. The method of claim 1, wherein in step (d) said enrichment element contained or carried by oligonucleotide B is an amplification and/or capture element.

7. The method of claim 6, wherein said amplification and capture elements are, respectively, an amplification primer binding site and an element for immobilisation to a solid phase.

8. The method of claim 1, wherein in step (d) oligonucleotide B is immobilised to a solid phase.

9. The method of a claim 1, wherein in step (d) oligonucleotide B further carries or contains a molecular tag.

10. The method of claim 1, wherein in step (e) said ligating of oligonucleotide B is to the end of said target fragment.

11. The method of claim 7, wherein in step (f) said target fragment in said probe-target fragment hybrid is immobilised to a solid phase by means of said immobilisation element.

12. The method of claim 1, wherein said non-specific annealing is by rendering the ends of the fragments sticky with respect to at least one end of the adaptor, and wherein said ligating of the adaptor to the fragments at the 3' ends, or at the 5' ends, of the strands of the fragments is by selective dephosphorylation of the fragments or the adaptor, respectively, prior to ligation.

13. The method of claim 1, wherein in step (a) said fragmenting a nucleic acid sample comprises separately fragmenting a plurality of nucleic acid samples, and step (b) comprises ligating to the fragments of which samples, respectively, variant adaptors carrying different molecular tags and pooling said adaptor-ligated fragmented nucleic acid samples.

14. The method of claim 1, wherein in step (d) said first target-specific part of oligonucleotide A comprises at least 10 nucleotides complementary in sequence to a single-stranded internal non-end portion of said at least partially single-stranded target fragment, and wherein said annealing of said probe to said target fragment is through hybridisation of said internal non-end portion to said first target-specific part of oligonucleotide A, causing the 5' end of the target fragment to form a substrate for flap endonucleolytic cleavage and further comprising cleaving said flap endonucleolytic cleavage substrate to produce a ligatable 5' end of said target fragment which is hybridised to oligonucleotide A of said probe.

15. The method of claim 14, wherein in step (e) said ligating of oligonucleotide B is to said ligatable 5' end of said target fragment.

16. The method of claim 1, wherein in step (f) said detecting or enriching is by means that increases the ratio of circular to linear molecules, further comprising, betweens steps (e) and (f), rendering double-stranded an end of at least the target fragment, being the end to which the probe is not ligated, which end will comprise a common nucleic acid adaptor sequence ligated to the fragments in step (b); non-target-specifically annealing said double-stranded end intramolecularly with the free, non-target fragment-bound end of the probe; and ligating oligonucleotide B of the probe-target fragment hybrid with the corresponding strand of said double-stranded end to circularise said hybrid.

17. The method of claim 16, wherein in step (f) said means that increases the ratio of circular to linear molecules is by exonuclease treatment and/or rolling circle amplification.

18. The method of claim 1, wherein in step (c) the rendering said fragments, including said target fragment, partially single-stranded is performed by 3' or 5' exonuclease digestion.

* * * * *

UNITED STATES PATENT AND TRADEMARK OFFICE
CERTIFICATE OF CORRECTION

PATENT NO. : 8,664,164 B2
APPLICATION NO. : 13/384990
DATED : March 4, 2014
INVENTOR(S) : Olof Ericsson et al.

Page 1 of 1

It is certified that error appears in the above-identified patent and that said Letters Patent is hereby corrected as shown below:

In the Specification

In column 1, line 7, delete "PCT/Ep2010/" and insert -- PCT/EP2010/ --, therefor.

In the Claims

In column 60, line 10, In Claim 9, after "method of" delete "a".

In column 60, line 50, in Claim 16, delete "betweens" and insert -- between --, therefor.

Signed and Sealed this
Seventeenth Day of June, 2014

Michelle K. Lee
*Deputy Director of the United States Patent and Trademark Office*